(12) United States Patent
Willot et al.

(10) Patent No.: US 11,479,565 B2
(45) Date of Patent: Oct. 25, 2022

(54) PROCESS FOR PREPARING SUBSTITUTED IMIDAZOLE DERIVATIVES

(71) Applicant: BAYER AKTIENGESELLSCHAFT, Leverkusen (DE)

(72) Inventors: Matthieu Willot, Duesseldorf (DE); Ruediger Fischer, Pulheim (DE); Dominik Hager, Monheim (DE); Laura Hoffmeister, Duesseldorf (DE); Marc Mosrin, Monheim am Rhein (DE); David Wilcke, Duesseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 17/283,270

(22) PCT Filed: Oct. 9, 2019

(86) PCT No.: PCT/EP2019/077307
§ 371 (c)(1),
(2) Date: Apr. 7, 2021

(87) PCT Pub. No.: WO2020/074560
PCT Pub. Date: Apr. 16, 2020

(65) Prior Publication Data
US 2021/0380611 A1    Dec. 9, 2021

(30) Foreign Application Priority Data

Oct. 11, 2018  (EP) .................................... 18199890

(51) Int. Cl.
*C07F 3/06* (2006.01)
(52) U.S. Cl.
CPC ...................... *C07F 3/06* (2013.01)
(58) Field of Classification Search
CPC .................................................... C07F 3/06
See application file for complete search history.

(56) References Cited

U.S. PATENT DOCUMENTS

| 10,766,909 B2 | 9/2020 | Mosrin et al. |
| 10,875,858 B2 | 12/2020 | Mosrin et al. |
| 2019/0202829 A1 | 7/2019 | Mosrin et al. |
| 2019/0330241 A1 | 10/2019 | Mosrin et al. |

(Continued)

FOREIGN PATENT DOCUMENTS

| EP | 2662365 A1 | 11/2013 |
| WO | 2013180193 A1 | 12/2013 |

(Continued)

OTHER PUBLICATIONS

Marc Mosrin "Regio-and Chemoselective Metalations of N-Heterocycles. Applications to the Synthesis of Biologically Active Compounds" Ph. D. thesis 2009 Ludwig-Maximilians-Universität München.*

(Continued)

*Primary Examiner* — David K O'Dell
(74) *Attorney, Agent, or Firm* — McBee Moore & Vanik IP, LLC

(57) ABSTRACT

The present invention relates to a process for preparing substituted imidazole derivatives of the formula (II)

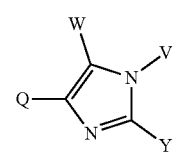

(II)

from compounds of the formula (I)

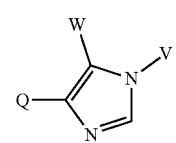

(I)

via intermediates of the formula (IVa) or (IVb)

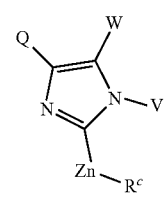

(IVa)

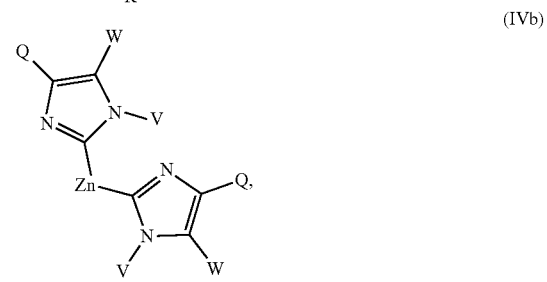

(IVb)

in which the structural elements shown in the formulae (I), (II), (IVa) and (IVb) have the meanings given in the description.
Furthermore, the invention relates to the intermediates of the formulae (IVa) and (IVb).

19 Claims, No Drawings

(56) References Cited

U.S. PATENT DOCUMENTS

| | | |
|---|---|---|
| 2019/0375766 A1 | 12/2019 | Mosrin et al. |
| 2020/0045976 A1 | 2/2020 | Wilcke et al. |
| 2020/0054017 A1 | 2/2020 | Wilcke et al. |

FOREIGN PATENT DOCUMENTS

| | | |
|---|---|---|
| WO | 2016039444 A1 | 3/2016 |
| WO | 2018007224 A1 | 1/2018 |
| WO | 2018033448 A1 | 2/2018 |
| WO | 2018050515 A1 | 3/2018 |
| WO | 2018130437 A1 | 7/2018 |
| WO | 2018130443 A1 | 7/2018 |
| WO | 2018141955 A1 | 8/2018 |

OTHER PUBLICATIONS

Crestey "Regioselective Functionalization of Purine Derivatives at Positions 8 and 6 Using Hindered TMP-Amide Bases of Zn and Mg" SYNTHESIS 2013, 45, 3029-3037.*

Morris, Kovacs and Ohe "Cyanogen Bromide" e-EROS Encyclopedia of Reagents for Organic Synthesis (2007), p. 5.*

Heuer, "Bildung und Strukturvon Bis(2,6-dimethoxyphenyl)nitramin," Zeitschriftfuer Naturforschung, B: Chemical Sciences (1989), 44(8), 911-16.*

Ciganek "Electrophilic Amination of Carbanions, Enolates, and Their Surrogates" Organic Reactions, vol. 72 2008.*

Graßl, S.; Chen, Y.-H.; Hamze, C.; Tullmann, C. P.; Knochel, P. Org. Lett. 2019, 21, 494.*

Schwarzer "Functionalization of 1,3,4-Oxadiazoles and 1,2,4-Triazoles via Selective Zincation or Magnesiation Using 2,2,6,6-Tetramethylpiperidyl Bases" Org. Lett. 2020, 22, 1899-1902.*

Balkenhohl, Moritz; Jangra, Harish; Makarov, Ilya S.; Yang, Shu-Mei; Zipse, Hendrik; et al Angewandte Chemie, International Edition (2020), 59(35), 14992-14999.*

Collins, I. et al. "A Convenient Synthesis of Highly Substituted 2-Pyridones" Tetrahedron Letters, Elsevier, May 21, 1999, pp. 4069-4072, vol. 40, No. 21, Amsterdam, NL.

Mosrin, Marc et al. "TMPZnCl-Li Cl: A New Active Selective Base for the Directed Zincation of Sensitive Aromatics and Heteroaromatics" Organic Letters, Apr. 16, 2009 (Apr. 16, 2009), pp. 1837-1840, vol. 11, No. 8.

Stathakis, Christos I. et al. "TMPZnOPiv-LiCl: A New Base for the Preparation of Air-Stable Solid Zinc Pivalates of Sensitive Aromatics and Heteroaromatics" Organic Letters, Mar. 15, 2013, pp. 1302-1305 vol. 15, No. 6, US.

Hlavinka, Mark L. Et al. "Zn(tmp) 2: A Versatile Base for the Selective Functionalization of C-H Bonds" ORGANOMETALLICS, Aug. 1, 2007. pp. 4105-4108, vol. 26. No. 17, US.

Mosrin, Marc et al. "Regio-and Chemoselective Multiple Functionalization of Pyrimidine Derivatives by Selective Magnesiations using TMPMgCl-LiCl" Organic Letters, Jun. 1, 2008, pp. 2497-2500, vol. 10, No. 12, US.

International Search Report of International Patent Application No. PCT/EP2019/077307, dated Nov. 5, 2019.

* cited by examiner

PROCESS FOR PREPARING SUBSTITUTED IMIDAZOLE DERIVATIVES

CROSS-REFERENCE TO RELATED APPLICATIONS

This application is the National Stage entry of International Application No. PCT/EP2019/077307, filed 9 Oct. 2019, which claims priority to European Patent Application No. 18199890.7, filed 11 Oct. 2018.

BACKGROUND

Field

The present invention relates to a process for preparing substituted imidazole derivatives of the formula (II)

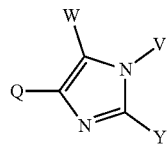

(II)

from compounds of the formula (I)

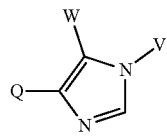

(I)

via intermediates of the formula (IVa) or (IVb)

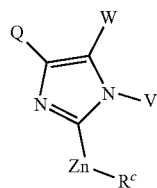

(IVa)

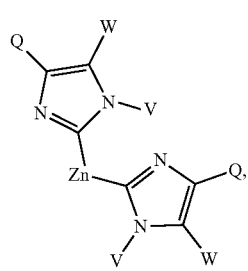

(IVb)

in which the structural elements shown in the formulae (I), (II), (IVa) and (IVb) have the definitions stated below.

Furthermore, the invention relates to the intermediates of the formulae (IVa) and (IVb).

Description of Related Art

Substituted imidazole derivatives of the formula (II) are of great industrial significance for the pharmaceutical and agrochemical industry and are, for example, important intermediates, inter alia, in the preparation of compounds that are effective as pesticides for example.

Corresponding imidazoles for use as pesticides and methods for the preparation thereof are described, for example, in WO 2013/180193, WO 2016/039444, WO 2018/130437 and WO 2018/130443.

The preparation methods that have been described in the prior art however include methods that are not economically implementable from an industrial point of view and/or have other disadvantages.

In particular, the regioselective introduction of the substituent to compounds of the formula (I) represents a major challenge. This is made particularly difficult by the two chemically very similar ring systems, which are coupled to each other in the compounds of the formula (I), and by the presence of other acidic protons in the compounds of the formula (I). The metallation and subsequent halogenation of such structures on the imidazole ring has not been described to date in the literature.

In particular in the case of lithium bases and magnesium bases usually employed, disadvantages are the low chemical yields, performing at very low temperatures and the difficult regio- and chemoselectivity of the deprotonation due to the high reactivity of these reagents. Sometimes a transmetallation with zinc salts, such as zinc chloride for example, is necessary in order to carry out further selective reactions such as Negishi cross-couplings as described in *Organic Letters* 2008, 10, 2497-2500. The preparation is therefore very expensive (many salts are formed) and unsuitable for industrial scale commercial processes.

With regard to the disadvantages outlined above, there is an urgent need for a simplified, industrially and economically performable method for preparing substituted imidazole derivatives, in particular of the formula (II). The substituted imidazole derivatives obtainable by this process sought are preferably to be obtained with good yield, high purity and in an economic manner.

Processes for preparing substituted imidazopyridines and their precursors using organozinc bases are described in WO 2018/007224, WO 2018/033448, WO 2018/050515 and WO 2018/141955.

SUMMARY

It has been found, surprisingly, that substituted imidazole derivatives of the formula (II), too, can be prepared advantageously in a process using an organozinc base, in particular even with high regio- and chemoselectivity and good yield.

The present invention accordingly provides a method for preparing compounds of the formula (II)

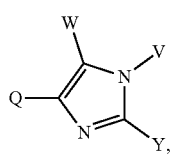

(II)

in which (Configuration 1)
Q represents a structural element

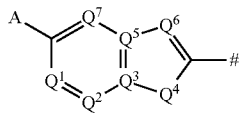

where the symbol # indicates the bond to the rest of the molecule and
$Q^1$ represents N or $CR^6$,
$Q^2$ represents N or $CR^6$,
$Q^3$ represents N or C,
$Q^4$ represents O, S, N, $CR^6$ or $NR^7$,
$Q^5$ represents N or C,
$Q^6$ represents N or CH and
$Q^7$ represents N or CH,
where at most five of the variables $Q^1$, $Q^2$, $Q^3$, $Q^4$, $Q^5$, $Q^6$ and $Q^7$ simultaneously represent nitrogen $Q^3$ and $Q^5$ and do not simultaneously represent N and
$R^6$ represents hydrogen, $(C_1-C_4)$-alkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_1)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_5)$-cycloalkyl, halo-$(C_3-C_6)$-cycloalkyl, $(C_1-C_4)$-alkylthio-$(C_1-C_4$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl and
$R^7$ represents $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_1-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl,
A represents hydrogen, cyano, halogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, $(C_1-C_4)$-alkylsulfonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulfonylamino, $(C_1-C_4)$-alkylamino, aminosulfonyl, $(C_1-C_4)$-alkylaminosulfonyl or di-$(C_1-C_4)$-alkylaminosulfonyl, or
A represents —O—$CF_2$—O— and, together with $Q^1$ and the carbon atom to which it is attached, forms a five-membered ring where $Q^1$ represents carbon,
W represents halogen or $S(O)_nR^8$, where
$R^8$ represents $(C_1-C_6)$-alkyl, $(C_1-C_6)$-cyanoalkyl, $(C_1-C_4)$-alkoxy-$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_8)$-cycloalkyl and n represents 0, 1 or 2,
V represents $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, cyano-$(C_3-C_8)$-cycloalkyl, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-alkylsulfonyl-$(C_1-C_6)$-haloalkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl or $(C_1-C_6)$-haloalkoxycarbonyl-$(C_1-C_6)$-alkyl and
Y represents halogen, cyano, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-haloalkylsulfinyl, $(C_1-C_4)$-alkylsulfonyl, $(C_1-C_4)$-haloalkylsulfonyl, SCN, $(C_1-C_4)$-alkylcarbonyl, $(C_1-C_4)$-haloalkylcarbonyl, $(C_1-C_4)$-alkoxycarbonyl, $(C_1-C_4)$-haloalkoxycarbonyl, aminocarbonyl, $(C_1-C_4)$-alkylaminocarbonyl, di-$(C_1-C_4)$-alkylaminocarbonyl, $(C_1-C_4)$-haloalkylaminocarbonyl, $(C_3-C_6)$-cycloalkylaminocarbonyl, aminothiocarbonyl, $(C_1-C_4)$-alkylaminothiocarbonyl, di-$(C_1-C_4)$-alkylaminothiocarbonyl, $(C_1-C_4)$-haloalkylaminothiocarbonyl, $(C_3-C_6)$-cycloalkylaminothiocarbonyl, amino, $(C_1-C_4)$-alkylamino, $(C_1-C_4)$-haloalkylamino, di-$(C_1-C_4)$-alkylamino, $(C_3-C_6)$-cycloalkylamino, $(C_1-C_4)$-alkylsulfonylamino, $(C_1-C_4)$-alkylcarbonylamino, $(C_1-C_4)$-haloalkylcarbonylamino, $(C_1-C_4)$-alkylcarbonyl-$(C_1-C_4)$-alkylamino, $(C_1-C_4)$-haloalkylcarbonyl-$(C_1-C_4)$-alkylamino, $(C_3-C_6)$-cycloalkylcarbonyl amino, $(C_3-C_6)$-cycloalkylcarbonyl-$(C_1-C_4)$-alkylamino, $(C_1-C_4)$-alkylthiocarbonylamino, $(C_1-C_4)$-haloalkylthiocarbonylamino, $(C_1-C_4)$-alkylthiocarbonyl-$(C_1-C_4)$-alkylamino, $(C_1-C_4)$-haloalkylthiocarbonyl-$(C_1-C_4)$-alkylamino, $(C_3-C_6)$-cycloalkylthiocarbonylamino, $(C_3-C_6)$-cycloalkylthiocarbonyl-$(C_1-C_4)$-alkylamino, $(C_2-C_4)$-alkenyl, $(C_2-C_4)$-haloalkenyl, $(C_2-C_4)$-cyanoalkenyl, $(C_3-C_6)$-cycloalkyl-$(C_2)$-alkenyl, $(C_2-C_4)$-alkynyl or $(C_2-C_4)$-haloalkynyl,
or represents $(C_3-C_6)$-cycloalkyl or $(C_5-C_6)$-cycloalkenyl, each of which is optionally mono- or polysubstituted by identical or different substituents, possible substituents being in each case: $(C_3-C_6)$-cycloalkyl, $(C_1-C_4)$-alkyl, $(C_1-C_4)$-haloalkyl, $(C_1-C_4)$-alkoxy, $(C_1-C_4)$-haloalkoxy, aminocarbonyl, aminothiocarbonyl, halogen or cyano,
or represents aryl or hetaryl, each of which is optionally mono- or polysubstituted by identical or different substituents, where (in the case of hetaryl) optionally at least one carbonyl group may be present and where possible substituents in each case are as follows: cyano, carboxyl, carboxyl, halogen, nitro, acetyl, hydroxy, amino, SCN, $SF_5$, tri-$(C_1-C_4)$-alkylsilyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, $(C_1-C_4)$-haloalkyl-$(C_3-C_6)$-cycloalkyl, halo-$(C_3-C_6)$-cycloalkyl, cyano-$(C_3-C_6)$-cycloalkyl, $(C_1-C_4)$-alkyl, $(C_1-C_4)$-cycloalkyl, $(C_1-C_4)$-cyanoalkyl, $(C_1-C_4)$-hydroxyalkyl, hydroxycarbonyl-$(C_1-C_4)$-alkoxy, $(C_1-C_4)$-alkoxycarbonyl-$(C_1-C_4)$-alkyl, $(C_1-C_4)$-alkoxy-$(C_1-C_4)$-alkyl, $(C_2-C_4)$-alkenyl, $(C_2-C_4)$-haloalkenyl, $(C_2-C_4)$-cyanoalkenyl, $(C_3-C_6)$-cycloalkyl-$(C_2)$-alkenyl, $(C_2-C_4)$-alkynyl, $(C_2-$ $C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxycarbonyl-($C_1$-$C_4$)-alkoxy, ($C_1$-$C_4$)-alkoxy-($C_1$-$C_4$)-alkoxyl, ($C_1$-$C_4$)-alkoxyimino, ($C_1$-$C_4$)-haloalkoxyimino, ($C_1$-$C_4$)-alkylthio, ($C_1$-$C_4$)-haloalkylthio, ($C_1$-$C_4$)-alkoxy-($C_1$-$C_4$)-alkylthio, ($C_1$-$C_4$)-alkylthio-($C_1$-$C_4$)-alkyl, ($C_1$-$C_4$)-haloalkylsulfinyl, ($C_1$-$C_4$)-alkoxy-($C_1$-$C_4$)-alkylsulfinyl, ($C_1$-$C_4$)-alkylsulfonyl, ($C_1$-$C_4$)-haloalkylsulfonyl, ($C_1$-$C_4$)-alkoxyl, ($C_1$-$C_4$)-alkylsulfonyl, ($C_1$-$C_4$)-alkylsulfonyl-($C_1$-$C_4$)-alkyl, ($C_1$-$C_4$)-alkylsulfonyloxy, ($C_1$-$C_4$)-haloalkylsulfonyloxy, ($C_1$-$C_4$)-alkylcarbonyl, ($C_1$-$C_4$)-haloalkylcarbonyl, ($C_1$-$C_4$)-alkylcarbonyloxy, ($C_1$-$C_4$)-alkoxycarbonyl, ($C_1$-$C_4$)-haloalkoxycarbonyl, aminocarbonyl, ($C_1$-$C_4$)-alkylaminocarbonyl, ($C_1$-$C_4$)-haloalkylaminocarbonyl, di-($C_1$-$C_4$)-alkylaminocarbonyl, ($C_1$-$C_4$)-alkenylaminocarbonyl, di-($C_2$-$C_4$)-alkenylaminocarbonyl, ($C_3$-$C_6$)-cycloalkylaminocarbonyl, ($C_1$-$C_4$)-alkylsulfonylamino, ($C_1$-$C_4$)-alkylamino, di-($C_1$-$C_4$)-alkylamino, ($C_1$-$C_4$)-haloalkylamino, ($C_3$-$C_6$)-cycloalkylamino, aminosulfonyl, ($C_1$-$C_4$)-alkylaminosulfonyl, di-($C_1$-$C_4$)-alkylaminosulfonyl, ($C_1$-$C_4$)-alkylsulfoximino, aminothiocarbonyl, ($C_1$-$C_4$)-alkylaminothiocarbonyl, di-($C_1$-$C_4$)-alkylaminothiocarbonyl, ($C_1$-$C_4$)-haloalkylaminothiocarbonyl, ($C_3$-$C_6$)-cycloalkylaminothiocarbonyl, ($C_1$-$C_4$)-alkylcarbonylamino, ($C_1$-$C_4$)-haloalkylcarbonylamino, ($C_1$-$C_4$)-alkylcarbonyl-($C_1$-$C_4$)-alkylamino, ($C_1$-$C_4$)-haloalkylcarbonyl-($C_1$-$C_4$)-alkylamino, ($C_3$-$C_6$)-cycloalkylcarbonylamino, ($C_3$-$C_6$)-cycloalkylcarbonyl-($C_1$-$C_4$)-alkylamino, ($C_1$-$C_4$)-alkylthiocarbonylamino, ($C_1$-$C_4$)-haloalkylthiocarbonylamino, ($C_1$-$C_4$)-alkylthiocarbonyl-($C_1$-$C_4$)-alkylamino, ($C_1$-$C_4$)-haloalkylthiocarbonyl-($C_1$-$C_4$)-alkylamino, ($C_3$-$C_6$)-cycloalkylthiocarbonylamino, ($C_3$-$C_6$)-cycloalkylthiocarbonyl-($C_1$-$C_4$)-alkylamino, hetaryl, oxohetaryl, halohetaryl, halooxohetaryl, cyanohetaryl, cyanooxohetaryl, ($C_1$-$C_4$)-haloalkylhetaryl or ($C_1$-$C_4$)-haloalkyloxohetaryl, characterized in that, in a first process step a), a compound of the formula (I)

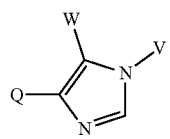

(I)

in Q, V and W each have the meanings given above, is reacted with an organozinc base of the structure ($NR^aR^b$)—Zn—$R^c$ or ($NR^aR^b$)$_2$—Zn, in which $R^c$ represents halogen or —O-pivaloyl and $R^a$ and $R^b$ together form a —(CH$_2$)$_4$—, —(CH$_2$)$_5$— or —(CH$_2$)$_2$O(CH$_2$)$_2$— group, where each of these groups may optionally be substituted by 1, 2, 3 or 4 $R^d$ radicals and $R^d$ is selected from the group consisting of methyl, ethyl, n-propyl and isopropyl, to give a compound of the formula (IVa) or the formula (IVb),

(IVa)

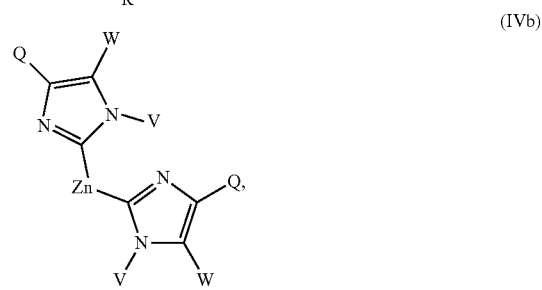

(IVb)

in which Q, V, W and $R^c$ each have the meanings given above, and this compound of the formula (IVa) or (IVb) is reacted in a second process step b) with a compound of the structure Y—X, in which X represents halogen and Y has the above-mentioned meaning, to give the compound of the formula (II).

DETAILED DESCRIPTION

Here, X preferably represents chlorine, bromine, iodine or fluorine, particularly preferably bromine or iodine, and very particularly preferably iodine.

The compounds of the formula (IVa) and (IVb) may also be present complexed with salts, where the salts are preferably alkali metal halides or alkaline earth metal halides, preferably lithium chloride and/or magnesium chloride and particularly preferably lithium chloride.

Preferably, at most four of the variables $Q^1$, $Q^2$, $Q^3$, $Q^4$, $Q^5$, $Q^6$ and $Q^7$ simultaneously represent nitrogen. Here, nitrogen is to be understood as meaning N and/or $NR^7$.

Preferred meanings of the Q, V, W and $R^c$ radicals included in the aforementioned formulae (I), (II), (IVa) and (IVb) of the method according to the invention are elucidated hereinafter, with more specific description of the organozinc base further down, and so the preferred configurations of the base are specified at that point.

(Configuration 2)

Q preferably represents a structural element from the group of Q1 to Q14,

Q1

Q2

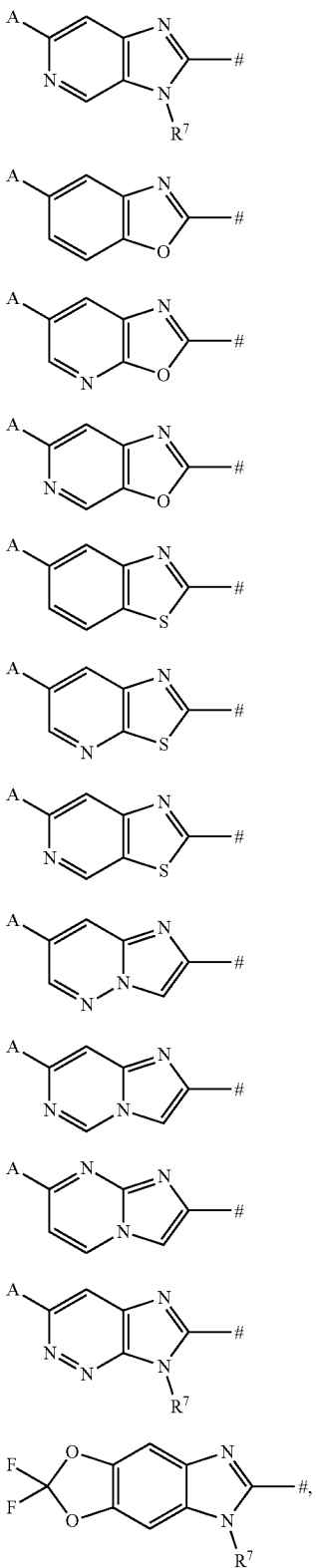

where
R[7] preferably represents $(C_1-C_4)$-alkyl, $(C_1-C_4)$-haloalkyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl, and A preferably represents fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulfinyl or trifluoromethylsulfonyl, W preferably represents halogen or $S(O)_nR^8$, where
R[8] preferably represents $(C_1-C_6)$-alkyl, $(C_1-C_6)$-cyanoalkyl, $(C_1-C_6)$-alkoxy-$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_8)$-cycloalkyl and
n preferably represents 0, 1 or 2, $R^c$ preferably represents halogen, in particular chlorine, bromine or iodine, V preferably represents $(C_1-C_6)$-alkyl, $(C_1-C_6)$-cyanoalkyl, $(C_1-C_6)$-alkoxy-$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_8)$-cycloalkyl and Y preferably represents halogen, cyano, $(C_1-C_4)$-haloalkyl, $(C_1-C_4)$-alkoxy, $(C_4-C_4)$-haloalkoxy, aminocarbonyl, $(C_1-C_4)$-alkylaminocarbonyl, di-$(C_4-C_4)$-alkylaminocarbonyl, $(C_1-C_4)$-haloalkylaminocarbonyl, $(C_2-C_6)$-cycloalkylaminocarbonyl, amino, $(C_1-C_4)$-alkylamino, $(C_1-C_4)$-haloalkylamino, $(C_3-C_6)$-cycloalkylamino, $(C_4-C_4)$-alkylsulfonylamino, $(C_1-C_4)$-alkylcarbonylamino, $(C_1-C_4)$-haloalkylcarbonylamino, $(C_1-C_4)$-alkylcarbonyl-$(C_1-C_2)$-alkylamino, $(C_1-C_4)$-haloalkylcarbonyl-$(C_1-C_2)$-alkylamino, $(C_3-C_6)$-cycloalkylcarbonylamino, $(C_3-C_6)$-cycloalkylcarbonyl-$(C_1-C_2)$-alkylamino, $(C_2-C_4)$-alkenyl, $(C_2-C_4)$-haloalkenyl, $(C_2-C_4)$-cyanoalkenyl or $(C_3-C_6)$-cycloalkyl-$(C_2)$-alkenyl, or represents $(C_3-C_6)$-cycloalkyl or $(C_5-C_6)$-cycloalkenyl, each of which is optionally mono- or polysubstituted by identical or different substituents, possible substituents being in each case: $(C_3-C_6)$-cycloalkyl, $(C_1-C_4)$-alkyl, $(C_1-C_4)$-haloalkyl, $(C_1-C_4)$-alkoxy, $(C_1-C_4)$-haloalkoxy, halogen or cyano, or represents phenyl, pyridyl, pyrimidyl, thiophenyl, (uranyl, pyrazolyl, pyrrolyl, thiazolyl, oxazolyl or imidazolyl, each of which is optionally mono- or polysubstituted by identical or different substituents, possible substituents being in each case: cyano, halogen, nitro, acetyl, hydroxy, amino, $SF_5-$, $(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_2)$-alkyl, $(C_2-C_4)$-alkenyl, $(C_2-C_4)$-haloalkenyl, $(C_2-C_4)$-cyanoalkenyl, $(C_3-C_6)$-cycloalkyl-$(C_2)$-alkenyl, $(C_2-C_4)$-alkynyl, $(C_2-C_4)$-haloalkynyl, $(C_2-C_4)$-cyanoalkynyl, $(C_1-C_4)$-alkoxy, $(C_1-C_4)$-haloalkoxy, $(C_1-C_4)$-cyanoalkoxy, $(C_1-C_4)$-alkoxy-$(C_1-C_2)$-alkoxy, $(C_1-C_4)$-alkoxyimino, $(C_1-C_4)$-haloalkoxyimino, $(C_1-C_4)$-alkylthio, $(C_1-C_4)$-haloalkylthio, $(C_1-C_4)$-alkylthio-$(C_1-C_2)$-alkyl, $(C_1-C_4)$alkylsulfinyl, $(C_1-C_4)$-haloalkylsulfinyl, $(C_1-C_4)$-alkylsulfonyl, $(C_1-C_4)$-haloalkylsulfonyl, alkylsulfonyloxyl, $(C_1-C_4)$-haloalkylsulfonyloxy, $(C_1-C_4)$-alkylcarbonyl, $(C_1-C_4)$-haloalkylcarbonyl, aminocarbonyl, $(C_1-C_4)$-alkylaminocarbonyl, $(C_1-C_4)$-haloalkylaminocarbonyl, di-$(C_1-C_4)$-alkylaminocarbonyl, $(C_3-C_6)$-cycloalkylaminocarbonyl, aminothiocarbonyl, $(C_1-C_4)$-alkylarninothiocarbonyl, di-$(C_1-C_4)$-alkylaminothiocarbonyl, $(C_1-C_4)$-haloalkylaminothiocarbonyl, $(C_3-C_6)$- cycloalkylaminothiocarbonyl, $(C_1-C_4)$-alkylsulfonylamino, $(C_1-C_4)$-alkylamino, di-$(C_1-C_4)$-alkylamino, $(C_1-C_4)$-haloalkylamino, $(C_3-C_6)$-cycloalkylamino, aminosulfonyl, $(C_1-C_4)$-alkylaminosulfonyl, di-$(C_1-C_4)$-alkylaminosulfonyl, $(C_1-C_4)$-alkylcarbonylamino, $(C_1-C_4)$-haloalkylcarbonylamino, $(C_1-C_4)$-alkylcarbonyl-$(C_1-C_2)$-alkylamino, $(C_1-C_2)$-haloalkylcarbonyl-$(C_1-C_4)$-alkylamino, $(C_3-C_6)$-cycloalkylcarbonylamino, $(C_3-C_6)$-cycloalkycarbonyl-$(C_1-C_2)$-alkylamino, $(C_1-C_4)$-alkylthiocarbonylamino, $(C_1-C_4)$-haloalkylthiocarbonylamino, $(C_1-C_4)$-alkylthrocarbonyl-$(C_1-C_2)$-alkylamino, $(C_1-C_4)$-haloalkylthiocarbonyl-$(C_1-C_2)$-alkylamino, $(C_3-C_6)$-cycloalkylthiocarbonylamino or $(C_3-C_6)$-cycloakylthiocarbonyl-$(C_1-C_2)$-alkylamino.

(Configuration 3)

Q particularly preferably represents a structural element from the group of Q2, Q3, Q4, Q10, Q11, Q13 and Q14, where $R^7$ particularly preferably represents $(C_1-C_4)$-alkyl or $(C_1-C_4)$-alkoxy-$(C_1-C_4)$-alkyl and A particularly preferably represents fluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulfinyl or trifluoromethylsulfonyl, W particularly preferably represents halogen or $S(O)_nR^8$, where $R^8$ particularly preferably represents methyl, ethyl, n-propyl or isopropyl, and n particularly preferably represents 0, 1 or 2, $R^c$ particularly preferably represents chlorine, V particularly preferably represents methyl, ethyl, n-propyl or isopropyl, and particularly preferably represents bromine, iodine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, or represents cyclopropyl, cyclobutyl, cyclopentyl, cyclohexyl, cyclopentenyl oder cyclohexenyl, each of which is optionally mono- or disubstituted by identical or different substituents, possible substituents being in each case: methyl, ethyl, n-propyl, isopropyl, cyclopropyl, difluoromethyl, trifluoromethyl, cyano, fluorine or chlorine, or represents phenyl, pyridin-2-yl, pyridin-3-yl, pyridin-4-yl, pyridazin-3-yl, pyridazin-4-yl, thien-2-yl, thien-3-yl, 1H-imidazol-5-yl, 1H-pyrazol-1-yl, 1H-pyrazol-3-yl, 1H-pyrazol-4-yl, 1H-pyrazol-5-yl, 1H-pyrrol-1-yl, 1H-pyrrol-2-yl, 1H-pyrrol-3-yl or 1-cyclohexenyl, each of which is optionally mono-, di- or trisubstituted by identical or different substituents, possible substituents being in each case: cyano, fluorine, chlorine, methyl, cyclopropyl, cyanomethyl, cyanoisopropyl, cyanocyclopropyl, trifluoromethyl, trifluoroethyl or aminocarbonyl.

(Configuration 4)

Q very particularly preferably represents the structural element Q3 or Q13, where $R^7$ very particularly preferably represents methyl or ethyl, in particular methyl, and A very particularly preferably represents trifluoromethyl or pentafluoroethyl, W very particularly preferably represents $S(O)_nR^8$, where $R^8$ very particularly preferably represents ethyl and n very particularly preferably represents 0 or 2, $R^c$ very particularly preferably represents chlorine, V very particularly preferably represents methyl or ethyl, in particular methyl, and Y very particularly preferably represents bromine, 5-cyanopyridin-2-yl or 6-chloropyridazin-3-yl.

The radical definitions and elucidations given above apply both to the end products and intermediates and to the starting materials in a corresponding manner. These radical definitions can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

In a further preferred embodiment of the invention, Q represents Q1 and $R^7$, A, W, n, $R^c$, V and Y have the meanings given in Configuration 1 or those given in Configuration 2 or those given in Configuration 3 or those given in Configuration 4 (Configuration 5).

In a further preferred embodiment of the invention, Q represents Q2 and $R^7$, A, W, $R^8$, n, $R^c$, V and Y have the meanings given in Configuration 1 or those given in Configuration 2 or those given in Configuration 3 or those given in Configuration 4 (Configuration 6).

In a further preferred embodiment of the invention, Q represents Q3 and $R^7$, A, W, $R^8$, n, $R^c$, V and Y have the meanings given in Configuration 1 or those given in Configuration 2 or those given in Configuration 3 or those given in Configuration 4 (Configuration 7).

In a further preferred embodiment of the invention, Q represents Q4 and A, W, $R^8$, n, $R^c$, V and Y have the meanings given in Configuration 1 or those given in Configuration 2 or those given in Configuration 3 or those given in Configuration 4 (Configuration 8).

In a further preferred embodiment of the invention, Q represents Q5 and A, W, $R^8$, n, $R^c$, V and Y have the meanings given in Configuration 1 or those given in Configuration 2 or those given in Configuration 3 or those given in Configuration 4 (Configuration 9).

In a further preferred embodiment of the invention, Q represents Q6 and A, W, $R^8$, n, $R^c$, V and Y have the meanings given in Configuration 1 or those given in Configuration 2 or those given in Configuration 3 or those given in Configuration 4 (Configuration 10).

In a further preferred embodiment of the invention, Q represents Q7 and A, W, $R^8$, n, $R^c$, V and Y have the meanings given in Configuration 1 or those given in Configuration 2 or those given in Configuration 3 or those given in Configuration 4 (Configuration 11).

In a further preferred embodiment of the invention, Q represents Q8 and A, W, $R^8$, n, $R^c$, V and Y have the meanings given in Configuration 1 or those given in Configuration 2 or those given in Configuration 3 or those given in Configuration 4 (Configuration 12).

In a further preferred embodiment of the invention, Q represents Q9 and A, W, $R^8$, n, $R^c$, V and have the meanings given in Configuration 1 or those given in Configuration 2 or those given in Configuration 3 or those given in Configuration 4 (Configuration 13).

In a further preferred embodiment of the invention, Q represents Q10 and A, W, $R^8$, n, $R^c$, V and Y have the meanings given in Configuration 1 or those given in Configuration 2 or those given in Configuration 3 or those given in Configuration 4 (Configuration 14).

In a further preferred embodiment of the invention, Q represents Q11 and A, W, $R^8$, n, $R^c$, V and have the meanings given in Configuration 1 or those given in Configuration 2 or those given in Configuration 3 or those given in Configuration 4 (Configuration 15).

In a further preferred embodiment of the invention, Q represents Q12 and A, W, $R^8$, n, $R^c$, V and Y have the meanings given in Configuration 1 or those given in Configuration 2 or those given in Configuration 3 or those given in Configuration 4 (Configuration 16).

In a further preferred embodiment of the invention, Q represents Q13 and $R^7$, A, W, $R^8$, n, $R^c$, V and Y have the meanings given in Configuration 1 or those given in Configuration 2 or those given in Configuration 3 or those given in Configuration 4 (Configuration 17).

In a further preferred embodiment of the invention, Q represents Q14 and $R^7$, W, $R^8$, n, $R^c$, V and Y have the meanings given in Configuration 1 or those given in Configuration 2 or those given in Configuration 3 or those given in Configuration 4 (Configuration 18).

In a particularly preferred embodiment of the invention, Q represents Q2, Q3, Q4, Q10, Q11, Q13 or Q14 and $R^7$, A, W, $R^8$, n, $R^c$, V and Y have the meanings given in Configuration 1 or those given in Configuration 2 or those given in Configuration 4 (Configuration 19).

In a particularly preferred embodiment of the invention, Q represents Q3 or Q13 and $R^7$, A, W, $R^8$, n, $R^c$, V and Y have the meanings given in Configuration 1 or those given in Configuration 2 or those given in Configuration 3 (Configuration 20).

Advantageously, the substituted imidazole derivatives of the formula (II) can be prepared by the process according to the invention with good yields and in high purity. Because of the very good functional group tolerance of zinc reagents, zinc bases are very attractive. Regio- and chemoselective metallations of imidazole derivatives in the presence of stoichiometric amounts of selective bases are made possible, even at elevated temperatures, without aryne elimination taking place or sensitive functional groups being attacked. The zinc compound formed as intermediate can subsequently be scavenged with various electrophiles, as described by way of example in Organic Letters 2009, 11, 1837-1840. These imidazole derivatives having novel substitution can then be further reacted as valuable synthons. Moreover, the process according to the invention allows further and/or more flexible derivatizations of starting material and product without having to constantly alter or adapt synthesis routes.

The process according to the invention can be elucidated by the following scheme (I):

Scheme (I)

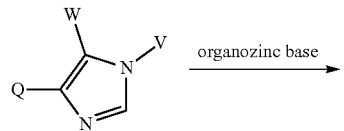
organozinc base →

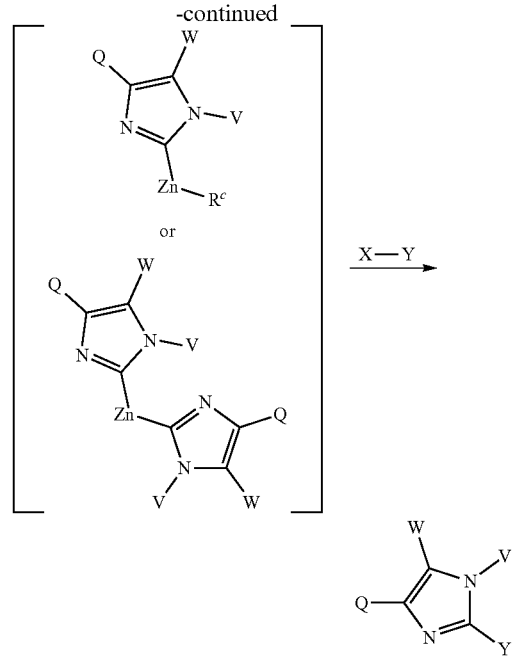

Here, Q, V, W, $R^c$, X and Y have the meanings given above. The compounds shown in brackets are the intermediate (formula (IVa) or formula (IVb)) which is reacted further to give the compound of the formula (II). Accordingly, the process according to the invention can be divided into the two process steps a) and b), step a) being the conversion of the compound of the formula (I) to the respective intermediate and step b) being the further conversion of the intermediate to the compound of the formula (II).

General Definitions

By definition, unless stated otherwise, halogen is selected from the group of fluorine, chlorine, bromine and iodine.

The term "halides" in connection with the present invention describes compounds between halogens and elements of other groups of the Periodic Table, where halide salts (ionic compounds (salts)) which consist of anions and cations because of the great difference in electronegativity between the elements involved and are held together by electrostatic interactions) or covalent halides (covalent compounds where the difference in electronegativity is not as great as in the aforementioned ionic compounds, but the bonds have charge polarity) may be present, depending on the nature of the chemical bond. Particular preference is given in accordance with the invention to halide salts.

In the context of the present invention, unless defined differently elsewhere, the term "alkyl", either on its own or else in combination with further terms, for example haloalkyl, is understood to mean a radical of a saturated, aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl.

The term "alkoxy", either on its own or else in combination with further terms, for example haloalkoxy, is understood in the present case to mean an O-alkyl radical, where the term "alkyl" is as defined above.

According to the invention, unless defined differently elsewhere, the term "aryl" is understood to mean an aromatic radical having 6 to 14 carbon atoms, preferably phenyl, naphthyl, anthryl or phenanthrenyl, particularly preferably phenyl.

Unless defined differently elsewhere, the term "arylalkyl" is understood to mean a combination of the radicals "aryl" and "alkyl" defined according to the invention, where the radical is generally attached via the alkyl group. Examples of these are benzyl, phenylethyl or α-methylbenzyl, benzyl being particularly preferred.

Unless defined differently elsewhere, "hetaryl" or "heteroaromatic ring" denotes a mono-, bi- or tricyclic heterocyclic group composed of carbon atoms and at least one heteroatom, where at least one ring is aromatic. Preferably, the hetaryl group contains 3, 4, 5, 6, 7 or 8 carbon atoms. Particular preference is given here to monocyclic groups of 3, 4, 5, 6, 7 or 8 carbon atoms and at least one heteroatom. The hetaryl group is particularly preferably selected from the series furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Halogen-substituted radicals, for example haloalkyl, are mono- or polyhalogenated, up to the maximum number of possible substituents. In the case of polyhalogenation, the halogen atoms may be identical or different. Unless stated otherwise, optionally substituted radicals may be mono- or polysubstituted, where the substituents in the case of polysubstitutions may be the same or different.

The term "pivaloyl" in the context of the present invention describes the deprotonated radical of pivalic acid (IX) having the empirical formula $(CH_3)_3C_7CO_2H$.

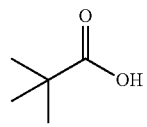

(IX)

"O-pivaloyl" correspondingly means that the bond of the pivaloyl radical is via the deprotonated oxygen atom of the acid group.

The synthesis of compounds of the formula (I) is known in principle to the person skilled in the art and is described, for example, in WO 2013/180193, WO 2016/039444, WO 2018/130437 and WO 2018/130443.

The conversion of the compounds of the formula (I) to compounds of the formula (IVa) or formula (IVb) in the first process step (step a)) is carried out in the presence of an organozinc base of the structure $(NR^aR^b)$—Zn—$R^c$ or $(NR^aR^b)_2$—Zn, in which (configuration B-1)

$R^c$ is as defined above (configuration 1) (and therefore represents halogen or —O-pivaloyl), $R^a$ and $R^b$ together form a —$(CH_2)_4$—, —$(CH_2)_5$— or —$(CH_2)_2O(CH_2)_2$— group, where each of these groups may optionally be substituted by 1, 2, 3 or 4 $R^d$ radicals and $R^d$ is selected from the group consisting of methyl, ethyl, n-propyl and isopropyl.

It is preferable that (configuration B-2)

$R^c$ is as defined above as preferred (configuration 2) (and is therefore —O-pivaloyl, chlorine, bromine or iodine), $R^a$ and $R^b$ together form a —$(CH_2)_5$— group, where each of these groups may optionally be substituted by 1, 2, 3 or 4 $R^d$ radicals and $R^d$ is selected from the group consisting of methyl and ethyl.

It is particularly preferable that (configuration B-3)

$R^c$ is as defined above as particularly preferred (configuration 6) (and is therefore chlorine) and $R^a$ and $R^b$ together form a —$(CH_2)_5$— group substituted by 4 methyl groups.

The radical definitions given above can be combined with one another as desired, i.e. including combinations between the respective preferred ranges.

In a very particularly preferred configuration of the base according to the invention, the structural element $(NR^aR^b)$ is tetramethylpiperidine (TMP) of formula (V).

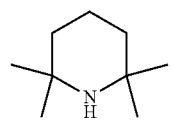

(V)

Organozinc bases very particularly preferred in accordance with the invention are accordingly characterized in that zinc is bound to TMP, especially in the form of zinc halide and most preferably in the form of zinc chloride. Bases of this kind have the following structure of the formula (VI) (configuration B-4)

$$(TMP)_x ZnCl_{2-x}, \quad (VI)$$

in which x is the number 1 or 2. Among these, preference is given in turn to bases where x=1 (configuration B-5) according to formula (VII):

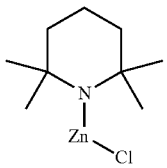

(VII)

In a further preferred embodiment of the process according to the invention, the organometallic base is present in conjunction with alkali metal halides or alkaline earth metal halides. This is especially true of bases of the for (VI) and (VII). Particularly preferred alkali metal halides or alkaline earth metal halides of this kind are lithium chloride and magnesium chloride, very particular preference being given to lithium chloride. Organometallic bases that are very particularly preferred in accordance with the invention are accordingly TMP ZnCl.LiCl or (TMP)$_2$ Zn.2LiCl or (TMP)$_2$ Zn.2LiCl MgCl$_2$ (configuration B-6). Most preferred is TMP ZnCl.LiCl (VIII; configuration B-7).

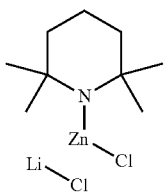

(VIII)

Specific combinations of compounds of the formulae (I), (II) and (IVa) or (IVb) with bases according to the invention are cited hereinafter by way of example in Table 1, these being employable in a process according to the invention. Since, in some configurations, the structural element R$^c$ is present both in the base according to the invention and in the compound of the formula (IVa), the narrowest definition applies to R$^c$ in each case.

TABLE 1

| Number | Compounds of the formulae (I), (II) and (IVa) or (IVb) | Base according to |
|---|---|---|
| 1 | Configuration 1 | Configuration B-1 |
| 2 | Configuration 1 | Configuration B-2 |
| 3 | Configuration 1 | Configuration B-3 |
| 4 | Configuration 1 | Configuration B-4 |
| 5 | Configuration 1 | Configuration B-5 |
| 6 | Configuration 1 | Configuration B-6 |
| 7 | Configuration 1 | Configuration B-7 |
| 8 | Configuration 2 | Configuration B-1 |
| 9 | Configuration 2 | Configuration B-2 |
| 10 | Configuration 2 | Configuration B-3 |
| 11 | Configuration 2 | Configuration B-4 |
| 12 | Configuration 2 | Configuration B-5 |
| 13 | Configuration 2 | Configuration B-6 |
| 14 | Configuration 2 | Configuration B-7 |
| 15 | Configuration 3 | Configuration B-1 |
| 16 | Configuration 3 | Configuration B-2 |
| 17 | Configuration 3 | Configuration B-3 |
| 18 | Configuration 3 | Configuration B-4 |
| 19 | Configuration 3 | Configuration B-5 |
| 20 | Configuration 3 | Configuration B-6 |
| 21 | Configuration 3 | Configuration B-7 |
| 22 | Configuration 4 | Configuration B-1 |
| 23 | Configuration 4 | Configuration B-2 |
| 24 | Configuration 4 | Configuration B-3 |
| 25 | Configuration 4 | Configuration B-4 |

TABLE 1-continued

| Number | Compounds of the formulae (I), (II) and (IVa) or (IVb) | Base according to |
|---|---|---|
| 26 | Configuration 4 | Configuration B-5 |
| 27 | Configuration 4 | Configuration B-6 |
| 28 | Configuration 4 | Configuration B-7 |
| 29 | Configuration 19 | Configuration B-1 |
| 30 | Configuration 19 | Configuration B-2 |
| 31 | Configuration 19 | Configuration B-3 |
| 32 | Configuration 19 | Configuration B-4 |
| 33 | Configuration 19 | Configuration B-5 |
| 34 | Configuration 19 | Configuration B-6 |
| 35 | Configuration 19 | Configuration B-7 |
| 36 | Configuration 20 | Configuration B-1 |
| 37 | Configuration 20 | Configuration B-2 |
| 38 | Configuration 20 | Configuration B-3 |
| 39 | Configuration 20 | Configuration B-4 |
| 40 | Configuration 20 | Configuration B-5 |
| 41 | Configuration 20 | Configuration B-6 |
| 42 | Configuration 20 | Configuration B-7 |

Preferably, the organometallic base is used in the method according to the invention in a total amount of 0.5 to 5.0 equivalents, preferably of 0.8 to 2.0 equivalents, further preferably of 1.0 to 1.5 equivalents and more preferably of 1.0 to 1.2 equivalents, based on the amount of material of compound of the formula (I), One advantage of the method according to the invention in this regard is that the organometallic base can be used in virtually stoichiometric amounts.

Depending on whether the structural element (NR$^a$R$^b$) is present once or twice in the organozinc base used, intermediate compounds of the formula (IVa) or of the formula (IVb) are formed in process step a).

The reaction of process step a) is particularly good at elevated temperatures. The reaction in process step a) is therefore generally conducted at a temperature between 0° C. and 110° C. and with increasing preference between 20° C. and 100° C., between 30° C. and 95° C., between 40° C. and 90° C., between 60° C. and 85° C., and most preferably between 70° C. and 85° C., for example at 80° C.

The reaction is typically conducted at standard pressure, but can also be conducted at elevated or reduced pressure.

Step a) generally takes place over a period of 5 min to 12 h, preferably 5 min to 10 h and particularly preferably 30 min to 2 h.

The conversion of the compounds of the formula (IVa) or (IVb) to compounds of the formula in the second process step (step b)) is effected in the presence of a compound X—Y in which X and Y each have the definitions given above.

Introduction of the Radical Y (Step b) for Y=Halogen):

In one variant of the invention, both X and Y represent halogen. In this case, X—Y is an interhalogen compound. Here, X and Y need not necessarily be the same halogen. For example, X may be iodine or bromine and Y may be chlorine, bromine or iodine. However, preferably the compound X—Y is elemental halogen, in particular F$_2$, Cl$_2$, or I$_2$. Particular preference is given to I$_2$ or Br$_2$, very particular preference to Br$_2$.

X—Y is preferably selected such that the radicals W and Y are different halogens, particularly preferably in the case that W represents fluorine, Y represents iodine, bromine or chlorine or W represents chlorine, Y represents iodine or bromine or W represents bromine, Y represents iodine.

Preferably, the compound X—Y is used in the process according to the invention in a total amount of 0.5 to 10 equivalents, preferably of 0.8 to 5.0 equivalents, further preferably of 1.0 to 2.5 equivalents and more preferably of 1.0 to 1.5 equivalents, based on the amount of material of compound of the formula (I).

The reaction in process step b) is generally carried out at a temperature between 0° C. and 80° C. and with increasing preference between 10° C. and 70° C., between 15° C. and C₀° C., between 20° C. and 50° C., between 20° C. and 40° C., and most preferably between 20° C. and 35° C., for example at room temperature or 25° C.

The reaction is typically conducted at standard pressure, but can also be conducted at elevated or reduced pressure.

In this variant of the invention, step b) generally takes place over a period of 5 min to 12 h, preferably 15 min to 10 h and particularly preferably 30 min to 2 h.

Introduction of the radical Y (step b) for Y≠halogen): In a further variant of the invention, the conversion of the compounds of the formula (IVa) or (IVb) into compounds of the formula (II) in the second method step (step b)) is carried out in the presence of a compound X—Y, in which Y has the meaning according to any of configurations 1 to 4, but does not represent halogen, and X preferably represents chlorine, bromine, iodine or fluorine (configuration (C-1)), particularly preferably bromine or iodine (C-2) and very particularly preferably iodine (C-3).

Listed by way of example in Table 2 below are compounds X—Y which may be used in a process according to the invention.

TABLE 2

| Number | Y | X |
|---|---|---|
| 1 | Configuration 1 without halogen | Configuration C-1 |
| 2 | Configuration 1 without halogen | Configuration C-2 |
| 3 | Configuration 1 without halogen | Configuration C-3 |
| 4 | Configuration 2 without halogen | Configuration C-1 |
| 5 | Configuration 2 without halogen | Configuration C-2 |
| 6 | Configuration 2 without halogen | Configuration C-3 |
| 7 | Configuration 3 without halogen | Configuration C-1 |
| 8 | Configuration 3 without halogen | Configuration C-2 |
| 9 | Configuration 3 without halogen | Configuration C-3 |
| 10 | Configuration 4 without halogen | Configuration C-1 |
| 11 | Configuration 4 without halogen | Configuration C-2 |
| 12 | Configuration 4 without halogen | Configuration C-3 |

The compounds of the formula (II) can preferably be prepared by cross-couplings, in particular by Negishi cross-coupling of the compounds of the formula (IVa) or (IVb) with the compounds X—Y in the presence of a catalyst such as described, for example, in *Angewandte Chemie International Edition* 2014, 53, 1430-1434.

In this case, the compound X—Y is preferably used in a total amount of 0.5 to 10 equivalents, preferably of 0.8 to 5.0 equivalents, further preferably of 1.0 to 2.5 equivalents and more preferably of 1.0 to 2.0 equivalents, based on the amount of material of compound of the formula (I).

In the case of a cross-coupling, step b) is preferably carried out in the presence of a catalyst. Preferably, the catalyst is a palladium compound or a nickel compound. More preferably, the catalyst is a palladium compound. Very particularly preferably, the catalyst is tetrakis(triphenylphosphine)palladium(0), abbreviated to Pd(PPH₃)₄, of the formula (III).

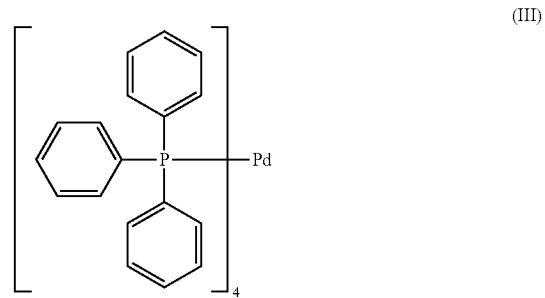

(III)

Typically, 2.5 to 25 mol % and preferably 5 to 20 mol % of catalyst, particularly tetrakis(triphenylphosphine)palladium(0), are used.

In this variant of the invention, step b) is generally carried out at a temperature between 0° C. and 120° C. and with increasing preference between 10° C. and 100° C. and especially preferably between 25° C. and 90° C.

In this variant of the invention, step b) generally takes place over a period of 5 min to 12 h, preferably 15 min to 10 h and particularly preferably 30 min to 4 h.

The reaction is typically conducted at standard pressure, but can also be conducted at elevated or reduced pressure.

The conversion according to the invention of the compounds of the formula (I) to compounds of the formula (IVa) or (IVb) and further to compounds of the formula (II) is preferably effected in the presence of an organic solvent in each case. Useful solvents in principle include all organic solvents which are inert under the reaction conditions employed and in which the compounds to be converted have adequate solubility. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); dimethylpropyleneurea (DMPU), halohydrocarbons and aromatic hydrocarbons, in particular chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorohenzene, 1,2-dichloroethane, chlorobenzene, bromobenzene, dichlorobenzene, in particular 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the solvents mentioned above such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tort-amyl methyl ether (TAME), 2-methyl-THE, toluene and 4-methoxybenzene.

Particularly preferred solvents are THF and N,N-dimethylformamide (DMF), very particular preference being given to THF.

The solvent may also be degassed (oxygen-free).

Preference is given to using the same solvent for both process steps a) and b). Alternative configurations of the invention in which different solvents are used for process steps a) and b) are likewise possible, however, in which case the solvents are then likewise preferably selected from the aforementioned solvents, and the respective solvents specified as being preferred, particularly preferred and especially preferred are applicable to the respective process step a) or b).

The desired compounds of the formula (II) can be isolated, for example, by aqueous workup the presence of saturated ammonium chloride or sodium thiosulfate solutions and/or subsequent chromatography. Such methods are known to those skilled in the art and also include crystallization from an organic solvent or solvent mixture.

A particularly preferred embodiment of the process according to the invention can be elucidated with reference to the following scheme (II):

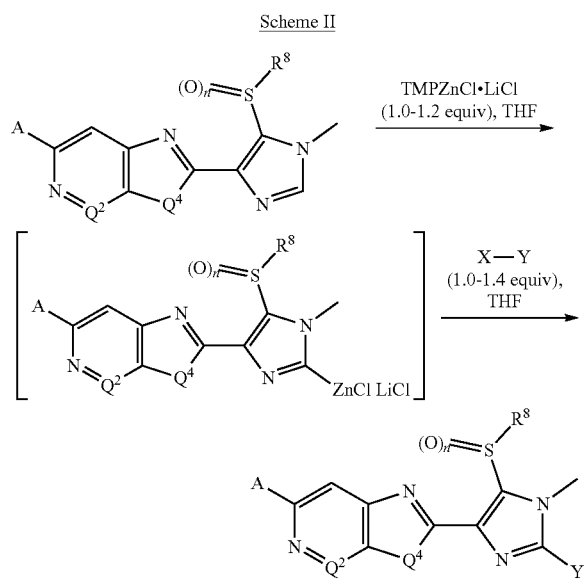

Here, $Q^2$, $Q^4$, $R^8$, n, A, X and Y have the meanings given above. The compound shown in brackets represents the corresponding intermediate of the formula (IVa) which is further reacted to give the product, a compound of the formula (II). Both reactions take place in THF as solvent, "Equiv" refers to the amount of equivalents of TMPZnCl. LiCl or X—Y used.

Moreover, the compounds of the formula (II) where Y=halogen can be converted in a further process step into compounds of the formula (II')

in which Q, V, W and Y have the abovementioned meanings and preferred ranges according to any of configurations 1 to 20, where Y does not represent halogen.

The conversion of the compounds of the formula (II) where Y=halogen into compounds of the formula (II') (step c) is preferably carried out by transition metal-mediated cross-couplings [cf. *Chem. Rev.* 1995, 95, 2457-2483; *Tetrahedron* 2002, 58, 9633-9695; *Metal-Catalyzed Cross-Coupling Reactions* (Eds.: A. de Meijere, Diederich), $2^{nd}$ ed., Wiley-VCH Weinheim, 2004] or by nucleophilic aromatic substitution (cf. the processes described in *Bioorganic and Medicinal Chemistry Letters* 2007, 17, 5825-5830 or U.S. Pat. No. 4,125,726).

For example, compounds of the formula (II) in which Y preferably represents bromine or iodine may be reacted with suitable boronic acids [Y—B(OH)$_2$] or boronic esters according to known methods (cf. WO 2012/143599, US 2014/094474, US 2014/243316, US 2015/284358 or *Journal of Organic Chemistry* 2004, 69, 8829-8835) in the presence of suitable catalysts from the series of transition metal salts to give compounds of the formula (II'). Here, examples of preferred coupling catalysts include palladium catalysts such as [1,1'-bis(diphenylphosphino)ferrocene]dichloropalladium(II), bis(triphenylphosphine)palladium(II) dichloride or tetrakis(triphenylphosphine)palladium. Suitable basic reaction auxiliaries used to conduct the processes are preferably carbonates of sodium, potassium or caesium. Some of the required boronic acid derivatives [Y—B(OH)$_2$] or boronic ester derivatives are known and/or commercially available, or they can be prepared by generally known methods (cf. *Boronic Acids* (eds.: D. G. Hall), 2nd ed., Wiley-VCH, Weinheim, 2011). In this case, the reaction is preferably conducted in a mixture of water and an organic solvent selected from customary solvents that are inert under the prevailing reaction conditions. Ethers such as tetrahydrofuran, dioxane or 1,2-dimethoxyethane are frequently used.

Alternatively, it is also possible to use stannane derivatives [Y—Sn(n-Bu)$_4$] as coupling partners (cf. US 2013/281433, WO 2004/099177 or WO 2016/071214). Some of the required stannane derivatives [Y—Sn(n-Bu)$_4$] are known and/or commercially available, or they can be prepared by generally known methods (cf. WO 2016/071214 or WO 2007/148093).

Coupling of the halogenated imidazole derivatives of the formula (II) with NH-containing heteroaromatics such as imidazoles or pyrazoles, optionally substituted as described above, to give compounds of the formula (II') can be conducted by reaction under basic conditions (e.g. with sodium hydride in dimethylformamide, cf. for example WO 2005/058898). Alternatively, the reaction can be carried out under an inert gas atmosphere by catalysis with copper(I) salts, copper(I) iodide for example, in the presence of a suitable ligand, e.g. (trans)-N,N'-dimethylcyclohexane-1,2-diamine or R-(+)-proline, and a suitable base, e.g. potassium carbonate or potassium phosphate, in a suitable solvent such as 1,4-dioxane or toluene (cf. e.g. WO 2016/109559).

The present invention further provides compounds of the formula (IVa)

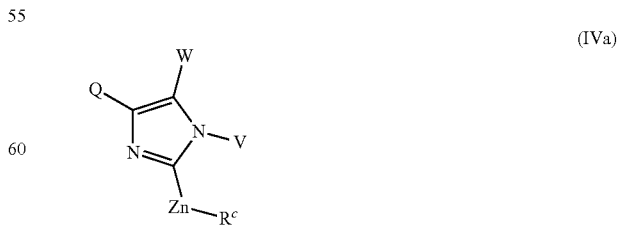

in which Q, V, $R^c$ and W have the definitions stated above and preferred configurations according to any of configurations 1 to 20.

The compounds of the formula (IVa) may also be present complexed with salts, where the salts are preferably alkali metal halides or alkaline earth metal halides, preferably chloride and/or magnesium chloride and particularly preferably lithium chloride.

Among the compounds of the formula (IVa), the following compounds are especially preferred, in which the respective compound can be present alone or as a lithium chloride complex:

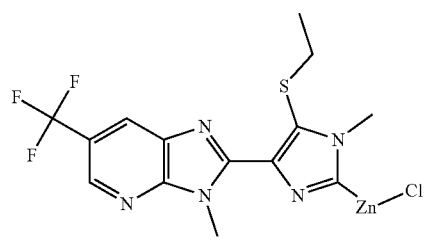

IVa-1

Chloro{5-(ethylsulfanyl)-1-methyl-4-
[3-methyl-6-(trifluoromethyl)-3H-
imidazo[4,5-b]pyridin-2-yl]-1H-
imidazol-2-yl}zinc

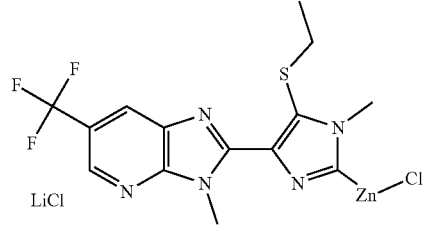

Chloro{5-(ethylsulfanyl)-1-methyl-4-[3-
methyl-6-(trifluoromethyl)-3H-
imidazo[4,5-b]pyridin-2-yl]-1H-
imidazol-2-yl}zinc/lithium chloride
complex

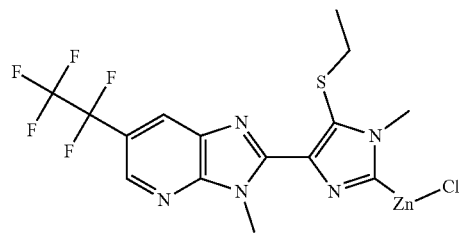

IVa-2

Chloro{5-(ethylsulfanyl)-1-methyl-4-
[3-methyl-6-(pentafluoroethyl)-3H-
imidazo[4,5-b]pyridin-2-yl]-1H-
imidazol-2-yl}zinc

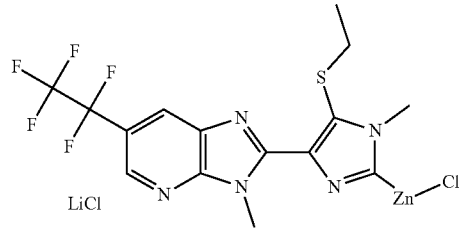

Chloro{5-(ethylsulfanyl)-1-methyl-4-[3-
methyl-6-(pentafluoroethyl)-3H-
imidazo[4,5-b]pyridin-2-yl]-1H-
imidazol-2-yl}zinc/lithium chloride
complex

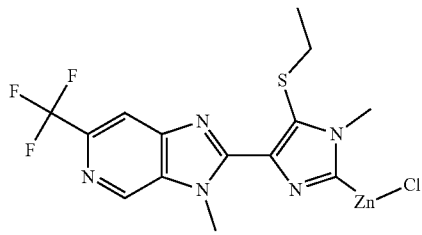

IVa-3

Chloro{5-(ethylsulfanyl)-1-methyl-4-
[3-methyl-6-(trifluoromethyl)-3H-
imidazo[4,5-c]pyridin-2-yl]-1H-
imidazol-2-yl}zinc

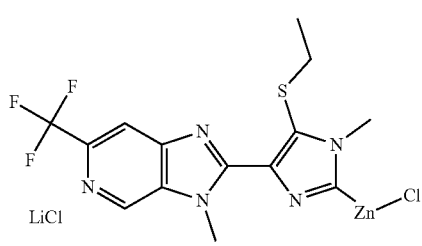

Chloro{5-(ethylsulfanyl)-1-methyl-4-[3-
methyl-6-(trifluoromethyl)-3H-
imidazo[4,5-c]pyridin-2-yl]-1H-
imidazol-2-yl}zinc/lithium chloride
complex

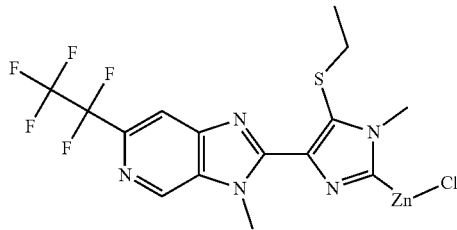

IVa-4

Chloro{5-(ethylsulfanyl)-1-methyl-4-
[3-methyl-6-(pentafluoroethyl)-3H-
imidazo[4,5-c]pyridin-2-yl]-1H-
imidazol-2-yl}zinc

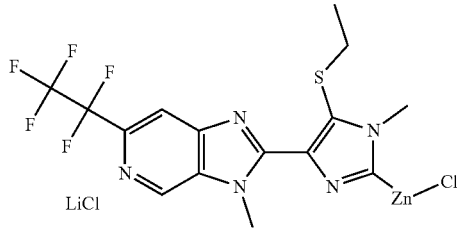

Chloro{5-(ethylsulfanyl)-1-methyl-4-[3-
methyl-6-(pentafluoroethyl)-3H-
imidazo[4,5-c]pyridin-2-yl]-1H-
imidazol-2-yl}zinc/lithium chloride
complex

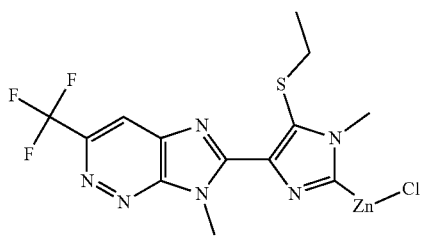

Chloro{5-(ethylsulfanyl)-1-methyl-4-
[7-methyl-3-(trifluoromethyl)-7H-
imidazo[4,5-c]pyridazin-6-yl]-1H-
imidazol-2-yl}zinc IVa-5

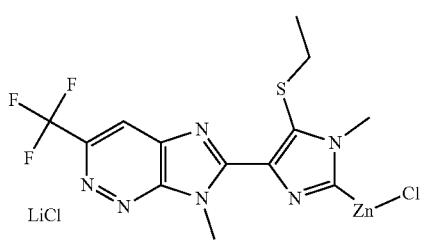

Chloro{5-(ethylsulfanyl)-1-methyl-4-[7-
methyl-3-(trifluoromethyl)-7H-
imidazo[4,5-c]pyridazin-6-yl]-1H-
imidazol-2-yl}zinc/lithium chloride
complex

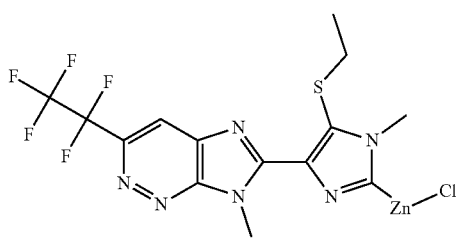

Chloro{5-(ethylsulfanyl)-1-methyl-4-
[7-methyl-3-(pentafluoroethyl)-7H-
imidazo[4,5-c]pyridazin-6-yl]-1H-
imidazol-2-yl}zinc IVa-6

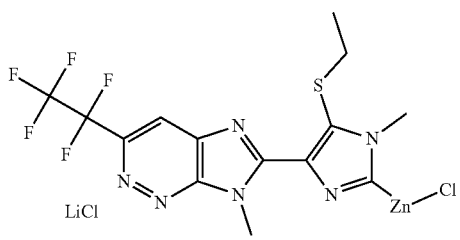

Chloro{5-(ethylsulfanyl)-1-methyl-4-[7-
methyl-3-(pentafluoroethyl)-7H-
imidazo[4,5-c]pyridazin-6-yl]-1H-
imidazol-2-yl}zinc/lithium chloride
complex

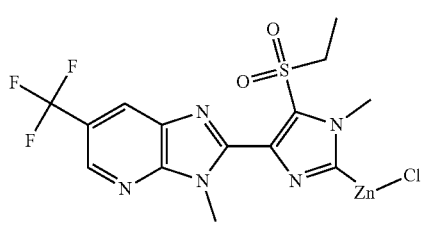

Chloro{5-(ethylsulfonyl)-1-methyl-4-
[3-methyl-6-(trifluoromethyl)-3H-
imidazo[4,5-b]pyridin-2-yl]-1H-
imidazol-2-yl}zinc IVa-7

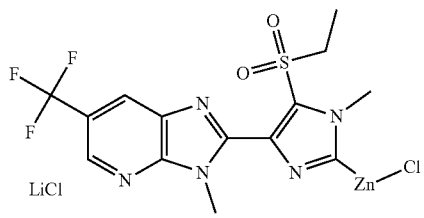

Chloro{5-(ethylsulfonyl)-1-methyl-4-[3-
methyl-6-(trifluoromethyl)-3H-
imidazo[4,5-b]pyridin-2-yl]-1H-
imidazol-2-yl}zinc/lithium chloride
complex

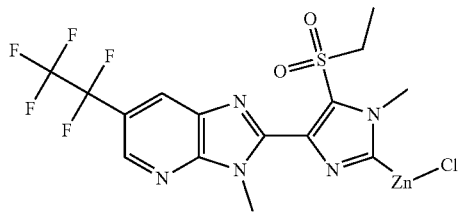

Chloro{5-(ethylsulfonyl)-1-methyl-4-
[3-methyl-6-(pentafluoroethyl)-3H-
imidazo[4,5-b]pyridin-2-yl]-1H-
imidazol-2-yl}zinc IVa-8

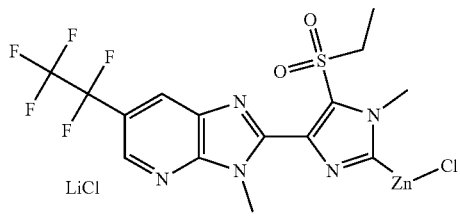

Chloro{5-(ethylsulfonyl)-1-methyl-4-[3-
methyl-6-(pentafluoroethyl)-3H-
imidazo[4,5-b]pyridin-2-yl]-1H-
imidazol-2-yl}zinc/lithium chloride
complex

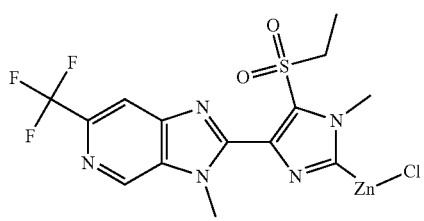

Chloro{5-(ethylsulfonyl)-1-methyl-4-
[3-methyl-6-(trifluoromethyl)-3H-
imidazo[4,5-c]pyridin-2-yl]-1H-
imidazol-2-yl}zinc IVa-9

-continued

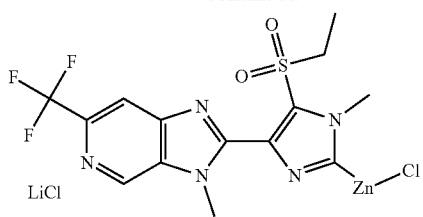

Chloro{5-(ethylsulfonyl)-1-methyl-4-[3-methyl-6-(trifluoromethyl)-3H-imidazo[4,5-c]pyridin-2-yl]-1H-imidazol-2-yl}zinc/lithium chloride complex IVa-10

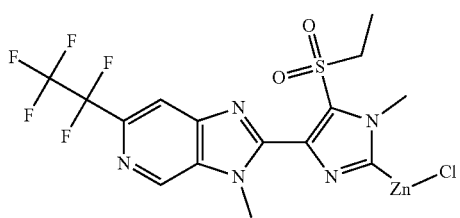

Chloro{5-(ethylsulfonyl)-1-methyl-4-[3-methyl-6-(pentafluoroethyl)-3H-imidazo[4,5-c]pyridin-2-yl]-1H-imidazol-2-yl}zinc

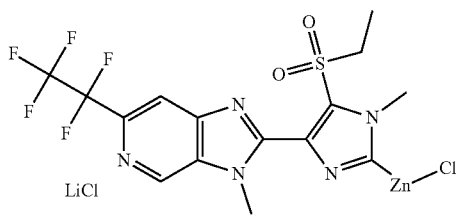

Chloro{5-(ethylsulfonyl)-1-methyl-4-[3-methyl-6-(pentafluoroethyl)-3H-imidazo[4,5-c]pyridin-2-yl]-1H-imidazol-2-yl}zinc/lithium chloride complex IVa-11

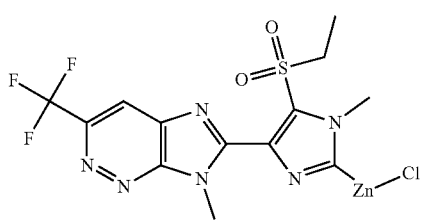

Chloro{5-(ethylsulfonyl)-1-methyl-4-[7-methyl-3-(trifluoromethyl)-7H-imidazo[4,5-c]pyridazin-6-yl]-1H-imidazol-2-yl}zinc

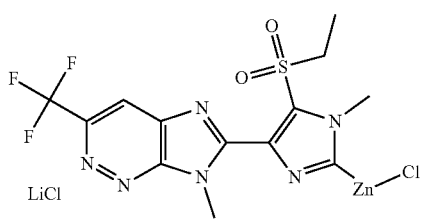

Chloro{5-(ethylsulfonyl)-1-methyl-4-[7-methyl-3-(trifluoromethyl)-7H-imidazo[4,5-c]pyridazin-6-yl]-1H-imidazol-2-yl}zinc/lithium chloride complex -continued IVa-12

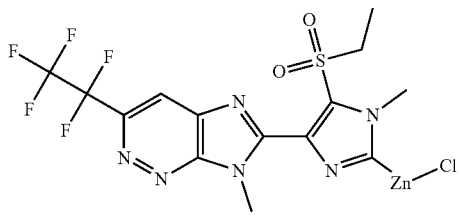

Chloro{5-(ethylsulfonyl)-1-methyl-4-[7-methyl-3-(pentafluoroethyl)-7H-imidazo[4,5-c]pyridazin-6-yl]-1H-imidazol-2-yl}zinc

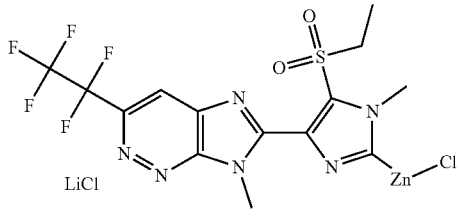

Chloro{5-(ethylsulfonyl)-1-methyl-4-[7-methyl-3-(pentafluoroethyl)-7H-imidazo[4,5-c]pyridazin-6-yl]-1H-imidazol-2-yl}zinc/lithium chloride complex The present invention further provides compounds of the formula (IVb)

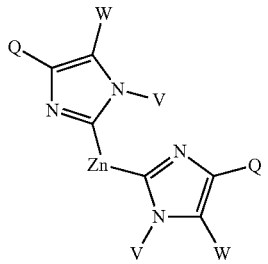

(IVb)

in which Q, V and W have the meanings given above and preferred configurations according to any of configurations 1 to 20.

The compounds of the formula (IVb) may also be present complexed with salts, where the salts are preferably alkali metal halides or alkaline earth metal halides, preferably lithium chloride and/or magnesium chloride as in structure (IVb-1) or (IVb-2) and particularly preferably lithium chloride (structure (IVb-1)).

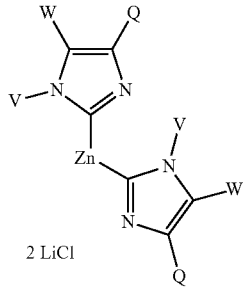

(IVb-1)

2 LiCl

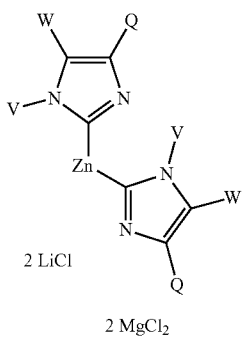

(IVb-2)

2 LiCl

2 MgCl$_2$

Q, V and W in formulae (IVb-1) and (IVb-2) have the meanings and preferred meanings given above according to any of configurations 1 to 20.

The present invention is elucidated in more detail by the examples which follow, although the examples should not be interpreted in a manner that restricts the invention.

Analytical Determinations

The analytical determination methods described below apply to all statements in the entire document unless the respective analytical determination method is specially described in the relevant text passage.

Mass Spectrometry

The determination of [M+H]$^+$ or M$^-$ by LC-MS under acidic chromatographic conditions was carried out using 1 ml of formic acid per litre of acetonitrile and 0.9 ml of formic acid per litre of Millipore water as mobile phases. The Zorbax Eclipse Plus C18 50 mm*2.1 mm, 1.8 μm column was used at a column oven temperature of 55° C.

Instruments:

LC-MS3: Waters UPLC with SQD2 mass spectrometer and SampleManager sample changer. Linear gradient from 0.0 to 1.70 minutes from 10% acetonitrile to 95% acetonitrile, from L70 to 2.40 minutes constant 95% acetonitrile, flow rate 0.85 ml/min.

LC-MS6 and LC-MS7: Agilent 1290 LC, Agilent MSD mass spectrometer, HTS PAL sample changer. Linear gradient from 0.0 to 1.80 minutes from 10% acetonitrile to 95% acetonitrile, from 1.80 to 2.50 minutes constant 95% acetonitrile, flow rate 1.0 mil/min.

The determination of [M+H]+$^+$ by LC-MS under neutral chromatographic conditions was carried out using acetonitrile and Millipore water with 79 mg/l ammonium carbonate as mobile phases.

Instruments:

LC-MS4: Waters IClass Acquity with QDA mass spectrometer and FTN sample changer (column Waters Acquity 1.7 μm 50 trim*2.1 mm, column oven temperature 45° C.). Linear gradient from 0.0 to 2.10 minutes from 10% acetonitrile to 95% acetonitrile, from 2.10 to 3.00 minutes constant 95% acetonitrile, flow rate 0.7 ml/min.

LC-MS5: Agilent 1100 LC system with MSD mass spectrometer and HTS PAL sample changer (column: Zorbax XDB C18 1.8 μm 50 mm*4.6 mm, column oven temperature 55° C.). Linear gradient from 0.0 to 4.25 minutes from 10% acetonitrile to 95% acetonitrile, from 4.25 to 5.80 minutes constant 95% acetonitrile, flow rate 2.0 ml/min.

In all cases, the retention time indices were determined from a calibration measurement of a homologous series of straight-chain alkan-2-ones having 3 to 16 carbons, where the index of the first alkanone was set to 300, the index of the last alkanone was set to 1600 and linear interpolation was carried out between the values of successive alkanones.

log P Values

The log values were determined according to EEC Directive 79/831 Annex V.A8 by HPLC (high-performance liquid chromatography) on a reversed-phase column (C18) using the following methods:

The log P[a] value is determined by LC-UV measurement in the acidic range using 0.9 mill formic acid in water and 1.0 ml/l formic acid in acetonitrile as mobile phases (linear gradient from 10% acetonitrile to 95% acetonitrile).

The log P[n] value is determined by LC-UV measurement in the neutral range using 79 mg/l ammonium carbonate in water and acetonitrile as mobile phases (linear gradient from 10% acetonitrile to 95% acetonitrile).

Calibration was carried out using a homologous series of straight-chain alkan-2-ones (having 3 to 16 carbon atoms) with known log values. The values between successive alkanones are determined by linear regression.

The $^1$H NMR spectra were measured with a Bruker Avance III 400 MHz spectrometer fitted with a 1.7 mm TCI sample head using tetramethylsilane as standard (0.00 ppm), of solutions in the solvents CD$_3$CN, CDCl$_3$ or d$_6$-DMSO. Alternatively, a Bruker Avarice III 600 MHz spectrometer fitted with a 5 mm CPNMP sample head or a Bruker Avance NEO 600 MHz spectrometer fitted with a 5 mm TCI sample head was employed for the measurements. In general, the measurements were carried out at a sample head temperature of 298 K. If other measurement temperatures were used, this is specifically mentioned.

The NMR data are stated in classic form (δ values, multiplet splitting, number of hydrogen atoms).

In each case, the solvent in which the NMR spectrum was recorded is stated.

Example 1

Synthesis of 6-[2-bromo-5-(ethylsulfanyl)-1-methyl-1H-imidazol-4-yl]-methyl-3-(trifluoromethyl)-7H-imidazo[4,5-e]pyridazine

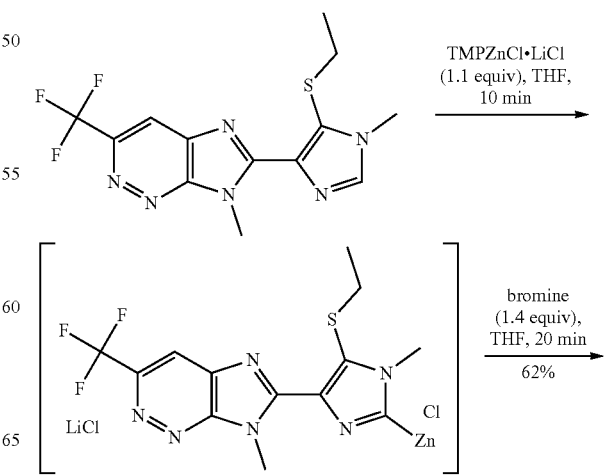

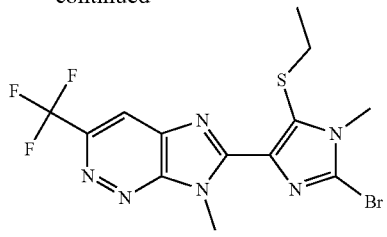

6-[5-(Ethylsulfanyl)-1-methyl-1H-imidazol-4-yl]-7-methyl-3-(trifluoromethyl)-7H-imidazo[4,5-c]pyridazine (1.60 g, 4.67 mmol) in anhydrous THF (10 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31M in THF, 3.92 ml, 5.14 mmol) was added dropwise and the mixture was stirred at 25° C. for 10 minutes. The reaction mixture was cooled to 0° C., then bromine (0.337 ml, 6.54 mmol) was added and the mixture was subsequently stirred at 25° C. for 20 minutes. Saturated aqueous ammonium chloride solution and sodium thiosulfate solution were added to the reaction mixture which was extracted three times with ethyl acetate and dried over anhydrous sodium sulfate. Following filtration, the solvent was removed under reduced pressure. The crude product was purified by chromatography, which gave 6-[2-bromo-5-(ethylsulfanyl)-1-methyl-1H-imidazol-4-yl]-7-methyl-3-(trifluoromethyl)-7H-imidazo[4,5-]pyridazine (1.26 g, 62%) as a white solid.

HPLC-MS: log P[a]=3.14; log P[n]=3.01; MH$^+$: 421;

$^1$H-NMR (d$_6$-DMSO): δ 8.565 (s, 1H), 4.275 (s, 3H), 3.78 (s, 3H), 3.05 (q, 2H), 1.13 (t, 3H).

Example 2

Synthesis of 6-[2-bromo-5-(ethylsulfanyl)-1-methyl-1H-imidazol-4-yl]-7-methyl-3-(pentafluoroethyl)-7H-imidazo[4,5-c]pyridazine

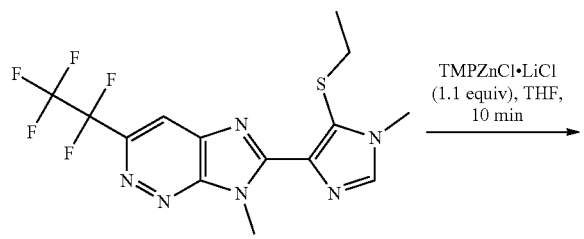

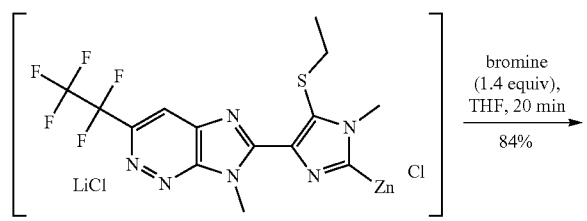

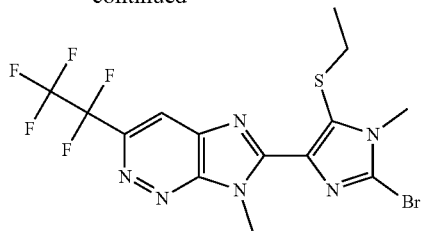

6-[5-(Ethylsulfanyl)-1-methyl-1H-imidazol-4-yl]-7-methyl-3-(pentafluoroethyl)-7H-imidazo[4,5-c]pyridazine (4.00 g, 10.2 mmol) in anhydrous THF (20 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31M in THF, 8.56 ml, 11.2 mmol) was added dropwise and the mixture was stirred at 25° C. for 10 minutes. The reaction mixture was cooled to 0° C., then bromine (0.435 ml, 14.3 mmol) was added and the mixture was subsequently stirred at 2.5° C. for 20 minutes. Saturated aqueous ammonium chloride solution and sodium thiosulfate, solution were added to the reaction mixture which was extracted three times with ethyl acetate and dried over anhydrous sodium sulfate. Following filtration, the solvent was removed under reduced pressure. The crude product was purified by chromatography, which gave 6-[2-bromo-5-(ethylsulfanyl)-1-methyl-1H-imidazol-4-yl]-7-methyl-3-(pentafluoroethyl)-7H-imidazo[4,5-c]pyridazine (4.36 g, 84%) as a white solid.

HPLC-MS: log P[a]=3.80; log P[n]=3.66; MH$^+$: 471;

$^1$H-NMR (d$_6$-DMSO): δ 8.59 (s, 1H), 4.28 (s, 3H), 3.79 (s, 3H), 3.06 (q, 2H), 1.12 (t, 3H).

Example 3

Synthesis of 6-[2-bromo-5-(ethylsulfonyl)-1-methyl-1H-imidazol-4-yl]-1-methyl-3-(pentafluoroethyl)-7H-imidazo[4,5-e]pyridazine

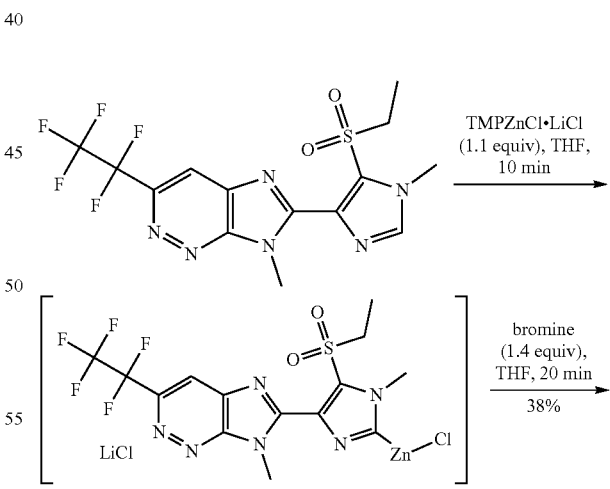

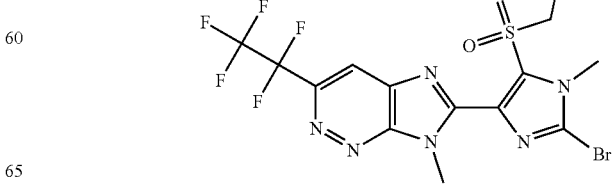

6-[5-(Ethylsulfonyl)-1-methyl-1H-imidazol-4-yl]-7-methyl-3-(pentafluoromethyl)-7H-imidazo[4,5-c]pyridazine (68.0 mg, 0.160 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl·LiCl) (1.30 M in THF, 0.136 ml, 0.176 mmol) was added dropwise and the mixture was stirred at 25° C. for 10 minutes. The reaction mixture was cooled to 0° C., then bromine (11 µl, 0.224 mmol) was added and the mixture was subsequently stirred at 25° C. for 20 minutes. Saturated aqueous ammonium chloride solution and sodium thiosulfate solution were added to the reaction mixture which was extracted three times with ethyl acetate and dried over anhydrous sodium sulfate. Following filtration, the solvent was removed under reduced pressure. The crude product was purified by chromatography, which gave 6-[2-bromo-5-(ethylsulfonyl)-1-methyl-1H-imidazol-4-yl]-7-methyl-3-(pentafluoroethyl)-7H-imidazo[4,5-c]pyridazine (40.0 mg, 50%) as a white solid.

HPLC-MS: log P[a]=2.80; log P[n]=2.76; MH⁺: 503;
¹H-NMR (d₆-DMSO): δ 8.74 (s, 1H), 4.06 (s, 3H), 3.94 (s, 3H), 3.78 (q, 2H), 1.29 (t, 3H).

Example 4

Synthesis of 2-[2-bromo-5-(ethylsulfanyl)-1-methyl-1H-imidazol-4-yl]-3-methyl-6-(pentafluoroethyl)-3H-imidazo[4,5-e]pyridine

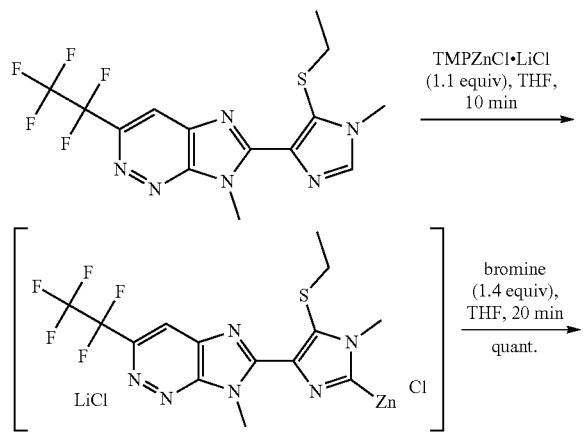

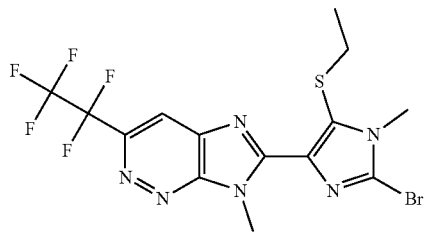

2-[5-(Ethylsulfanyl)-1-methyl-1H-imidazol-4-yl]-3-methyl-6-(pentafluoroethyl)-3H-imidazo[4,5-c]pyridine (86.5 mg, 0.221 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl·LiCl) (1.30 M in THF, 0.187 ml, 0.243 mmol) was added dropwise and the mixture was stirred at 25° C. for 10 minutes. The reaction mixture was cooled to 0° C., then bromine (16 µl, 0.309 mmol) was added and the mixture was subsequently stirred at 25° C. for 20 minutes. Saturated aqueous ammonium chloride solution and sodium thiosulfate solution were added to the reaction mixture which was extracted three times with ethyl acetate and dried over anhydrous sodium sulfate. Following filtration, the solvent was removed under reduced pressure. The crude product was purified by chromatography, which gave 2-[2-bromo-5-(ethylsulfanyl)-1-methyl-1H-imidazol-4-yl]-3-methyl-6-(pentafluoroethyl)-3H-imidazo[4,5-c]pyridine (128 mg, quant.) as a white solid.

HPLC-MS: log P[a]=3.63; log P[n]=3.51; MH⁺: 470;
¹H-NMR (d₆-DMSO: δ 9.17 (s, 1H), 8.21 (s, 1H), 4.15 (s, 3H), 3.76 (s, 3H), 3.01 (q, 2H), 1.11 (t, 3H).

Example 5

Synthesis of 6-[2(6-chloropyridazin-3-yl)-5-(ethylsulfanyl)-1-methyl-1H-imidazol-4-yl]-7-methyl-3-(pentafluoroethyl)-7H-imidazo[4,5-e]pyridazine

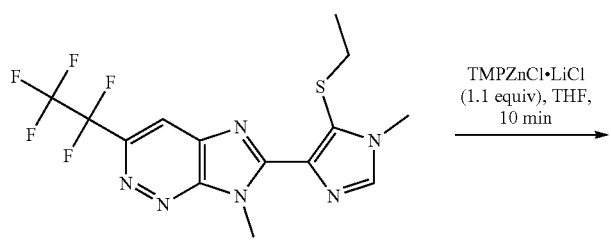

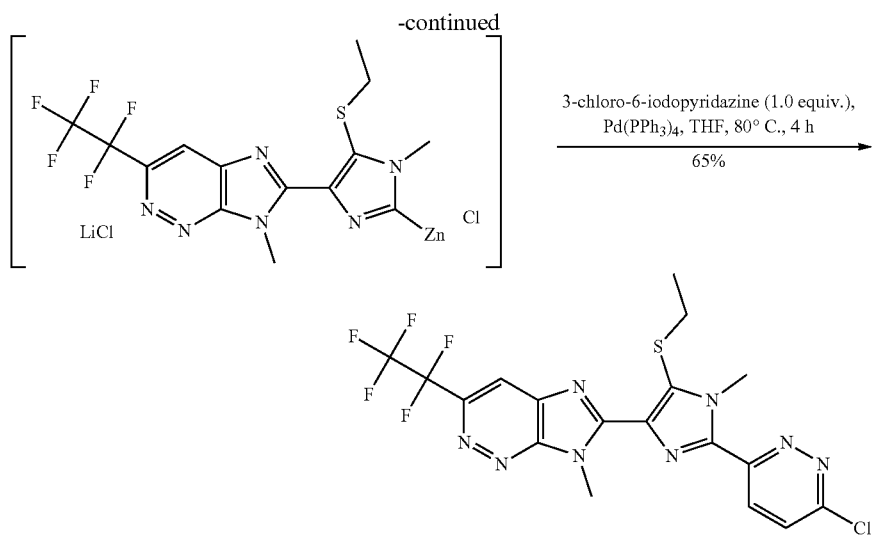

6-[5-(Ethylsulfonyl)-1-methyl-1H-imidazol-4-yl]-7-methyl-3-(pentafluoroethyl)-7H-imidazo[4,5-c]pyridazine (100 mg, 0.255 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl.LiCl) (1.31 M in THF, 0.214 ml, 0.280 mmol) was added dropwise and the mixture was stirred at 25° C. for 10 minutes. A solution of 3-chloro-6-iodopyridazine (61.3 mg, 0.255 mmol) in anhydrous THF (10 ml) and tetrakis (triphenylphosphine)palladium(0) (29.5 mg, 0.025 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-[2-(6-chloropyridazin-3-yl)-5-(ethylsulfanyl)-1-methyl-1H-imidazol-4-yl]-7-methyl-3-(pentafluoroethyl)-7H-imidazo[4,5-c]pyridazine (83.3 mg, 65%) as a white solid.

HPLC-MS: log P[a]=4.13; log P[n]=4.01; MH$^+$: 505;

$^1$H-NMR (d$_6$-DMSO); δ 8.63 (s, 1H), 8.54 (d, 1H), 8.14 (d, 1H), 4.41 (s, 3H), 4.26 (s, 3H), 3.14 (q, 2H), 1.18 (t, 3H).

Example 6

Synthesis of 6-{5-(ethylsulfanyl)-1-methyl-4-[7-methyl-3-(pentafluoroethyl)-7H-imidazo[4,5-e] pyridazin-6-yl]-1H-imidazol-2-yl}nicotinonitrile

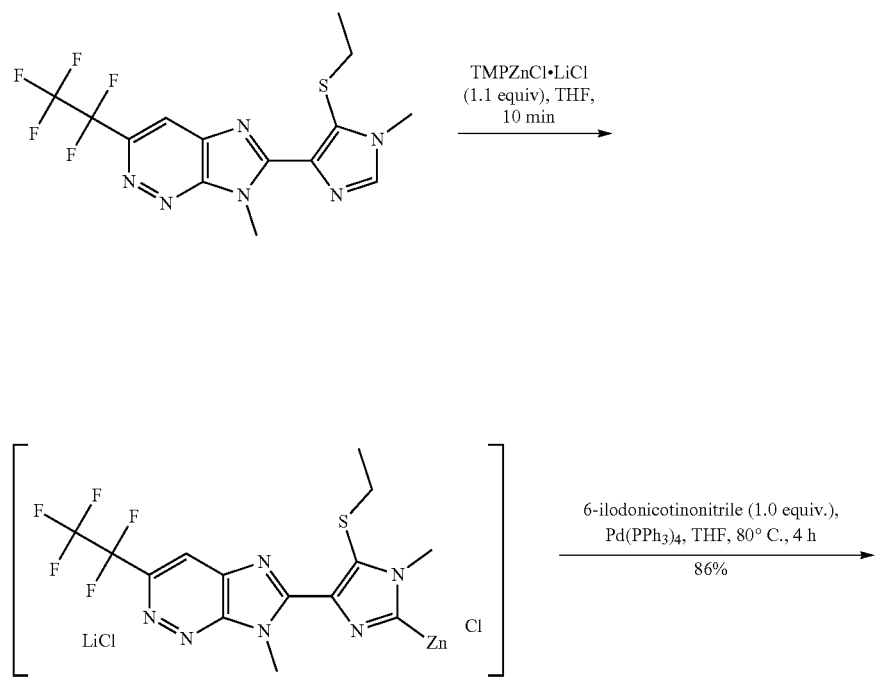

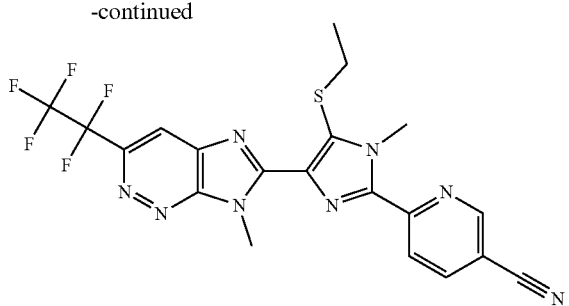

6-[5-(Ethylsulfonyl)-1-methyl-1H-imidazol-4-yl]-7-methyl-3-(pentafluoroethyl)-7H-imidazo[4,5-c]pyridazine (100 mg, 0.255 mmol) in anhydrous THF (5 ml) was initially charged in a dry, argon-filled Schlenk flask, equipped with a magnetic stirrer bar and a septum. Zinc chloride-2,2,6,6-tetramethylpiperidin-1-ide lithium chloride complex (TMPZnCl·LiCl) (1.31 M in THF, 0.214 ml, 0.280 mmol) was added dropwise and the mixture was stirred at 25° C. for 10 minutes. A solution of 6-iodonicotinonitrile (58.6 mg, 0.255 mmol) in anhydrous THF (10 ml) and tetrakis(triphenylphosphine)palladium(0) (29.5 mg, 0.025 mmol) were added, and the reaction mixture was then stirred at 80° C. for 4 hours. The reaction mixture was cooled to 25° C., saturated aqueous ammonium chloride solution and sodium thiosulfate solution were added, the mixture was extracted three times with ethyl acetate and the extracts were dried over anhydrous sodium sulfate. Following filtration, the solvent was removed under reduced pressure. The crude product was purified by chromatography, which gave 6-{5-(ethylsulfanyl)-1-methyl-4-[7-methyl-3-(pentafluoroethyl)-7H-imidazo[4,5-c]pyridazin-6-yl]-1H-imidazol-2-yl}nicotinonitrile (109 mg, 86%) as a white solid.

HPLC-MS: log P[a]=4.32; log P[n]=4.20; MH$^+$: 495:

$^1$H-NMR (d$_6$-DMSO): δ 9.19 (m, 1H), 8.62 (s, 1H), 8.51 (m, 1H), 8.46 (m, 1H), 4.42 (s, 3H), 4.265 (s, 3H), 3.13 (q, 2H), 1.16 (t, 3H).

The invention claimed is:

1. A process for preparing a compound of formula (II)

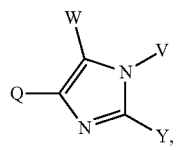

(II)

in which

Q represents a structural element

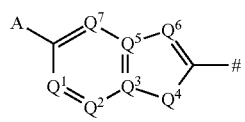

where the symbol # indicates the bond to the rest of the molecule and $Q^1$ represents N or $CR^6$,
$Q^2$ represents N or $CR^6$,
$Q^3$ represents C,
$Q^4$ represents O, S, N, or $NR^7$,
$Q^5$ represents C,
$Q^6$ represents N and
$Q^7$ represents CH, where $R^6$ represents hydrogen, ($C_1$-$C_4$)-alkyl, ($C_1$-$C_4$)-haloalkyl, ($C_1$-$C_4$)-cyanoalkyl, ($C_1$-$C_4$)-alkoxy-($C_1$-$C_4$)-alkyl, ($C_1$-$C_4$)-haloalkoxy-($C_1$-$C_4$)-alkyl, ($C_2$-$C_4$)-alkenyl, ($C_2$-$C_4$)-alkenyloxy-($C_1$-$C_4$)-alkyl, ($C_2$-$C_4$)-haloalkenyloxy-($C_1$-$C_4$)-alkyl, ($C_2$-$C_4$)-haloalkenyl, ($C_2$-$C_4$)-cyanoalkenyl, ($C_2$-$C_4$)-alkynyl, ($C_2$-$C_4$)-alkynyloxy-($C_1$-$C_4$)-alkyl, ($C_2$-$C_4$)-haloalkynyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkylthio-($C_1$-$C_4$)-alkyl, ($C_1$-$C_4$)-alkylsulfinyl-($C_1$-$C_4$)-alkyl, ($C_1$-$C_4$)-alkylsulfonyl-($C_1$-$C_4$)-alkyl or ($C_1$-$C_4$)-alkylcarbonyl-($C_1$-$C_4$)-alkyl and $R^7$ represents ($C_1$-$C_4$)-alkyl, ($C_1$-$C_4$)-haloalkyl, ($C_1$-$C_4$)-cyanoalkyl, ($C_1$-$C_4$)-alkoxy-($C_1$-$C_4$)-alkyl, ($C_1$-$C_4$)-haloalkoxy-($C_1$-$C_4$)-alkyl, ($C_2$-$C_4$)-alkenyl, ($C_2$-$C_4$)-alkenyloxy-($C_1$-$C_4$)-alkyl, ($C_2$-$C_4$)-haloalkenyloxy-($C_1$-$C_4$)-alkyl, ($C_2$-$C_4$)-haloalkenyl, ($C_2$-$C_4$)-cyanoalkenyl, ($C_2$-$C_4$)-alkynyl, ($C_2$-$C_4$)-alkynyloxy-($C_1$-$C_4$)-alkyl, ($C_2$-$C_4$)-haloalkynyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkylthio-($C_1$-$C_4$)-alkyl, ($C_1$-$C_4$)-alkylsulfinyl-($C_1$-$C_4$)-alkyl, ($C_1$-$C_4$)-alkylsulfonyl-($C_1$-$C_4$)-alkyl or ($C_1$-$C_4$)-alkylcarbonyl-($C_1$-$C_4$)-alkyl, A represents hydrogen, cyano, halogen, ($C_1$-$C_4$)-alkyl, ($C_1$-$C_4$)-haloalkyl, ($C_2$-$C_4$)-alkenyl, ($C_2$-$C_4$)-haloalkenyl, ($C_2$-$C_4$)-alkynyl, ($C_2$-$C_4$)-haloalkynyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, ($C_1$-$C_4$)-alkoxy, ($C_1$-$C_4$)-haloalkoxy, ($C_1$-$C_4$)-alkoxyimino, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, ($C_1$-$C_4$)-alkylcarbonyl, ($C_1$-$C_4$)-haloalkylcarbonyl, aminocarbonyl, ($C_1$-$C_4$)-alkylaminocarbonyl, di-($C_1$-$C_4$)-alkylaminocarbonyl, ($C_1$-$C_4$)-alkylsulfonylamino, ($C_1$-$C_4$)-alkylamino, di-($C_1$-$C_4$)-alkylamino, aminosulfonyl, ($C_1$-$C_4$)-alkylaminosulfonyl or di-($C_1$-$C_4$)-alkylaminosulfonyl, or A represents —O—$CF_2$—O— and, together with $Q^1$ and the carbon atom to which it is attached, forms a five-membered ring where $Q^1$ represents carbon, W represents halogen or $S(O)_n R^8$, where $R^8$ represents ($C_1$-$C_6$)-alkyl, ($C_1$-$C_6$)-cyanoalkyl, ($C_1$-$C_6$)-alkoxy-($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl or ($C_3$-$C_8$)-cycloalkyl and n represents 0, 1 or 2, V represents $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, cyano-$(C_3-C_8)$-cycloalkyl, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-alkyl, $(C_1-C_6)$-haloalkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl or $(C_1-C_6)$-haloalkoxycarbonyl-$(C_1-C_6)$-alkyl and Y represents halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, SCN, $(C_1-C_4)$-alkylcarbonyl, $(C_1-C_4)$-haloalkylcarbonyl, $(C_1-C_4)$-alkoxycarbonyl, $(C_1-C_4)$-haloalkoxycarbonyl, $(C_1-C_4)$-alkylaminocarbonyl, di-$(C_1-C_4)$-alkylaminocarbonyl, $(C_1-C_4)$-haloalkylaminocarbonyl, $(C_3-C_6)$-cycloalkylaminocarbonyl, $(C_1-C_4)$-alkylaminothiocarbonyl, di-$(C_1-C_4)$-alkylaminothiocarbonyl, $(C_1-C_4)$-haloalkylaminothiocarbonyl, $(C_3-C_6)$-cycloalkylaminothiocarbonyl, $(C_1-C_4)$-alkylamino, $(C_1-C_4)$-haloalkylamino, di-$(C_1-C_4)$-alkylamino, $(C_3-C_6)$-cycloalkylamino, $(C_1-C_4)$-alkylsulfonylamino, $(C_1-C_4)$-alkylcarbonylamino, $(C_1-C_4)$-haloalkylcarbonylamino, $(C_1-C_4)$-alkylcarbonyl-$(C_1-C_4)$-alkylamino, $(C_1-C_4)$-haloalkylcarbonyl-$(C_1-C_4)$-alkylamino, $(C_3-C_6)$-cycloalkylcarbonylamino, $(C_3-C_6)$-cycloalkylcarbonyl-$(C_1-C_4)$-alkylamino, $(C_1-C_4)$-alkylthiocarbonylamino, $(C_1-C_4)$-haloalkylthiocarbonylamino, $(C_1-C_4)$-alkylthiocarbonyl-$(C_1-C_4)$-alkylamino, $(C_1-C_4)$-haloalkylthiocarbonyl-$(C_1-C_4)$-alkylamino, $(C_3-C_6)$-cycloalkylthiocarbonylamino, $(C_3-C_6)$-cycloalkylthiocarbonyl-$(C_1-C_4)$-alkylamino, $(C_2-C_4)$-alkenyl, $(C_2-C_4)$-haloalkenyl, $(C_2-C_4)$-cyanoalkenyl, $(C_3-C_6)$-cycloalkyl-$(C_2)$-alkenyl, $(C_2-C_4)$-alkynyl or $(C_2-C_4)$-haloalkynyl, or represents $(C_3-C_6)$-cycloalkyl or $(C_5-C_6)$-cycloalkenyl, each of which is optionally mono- or polysubstituted by identical or different substituents, possible substituents being in each case: $(C_3-C_6)$-cycloalkyl, $(C_1-C_4)$-alkyl, $(C_1-C_4)$-haloalkyl, $(C_1-C_4)$-alkoxy, $(C_1-C_4)$-haloalkoxy, aminocarbonyl, aminothiocarbonyl, halogen or cyano, or represents aryl or hetaryl, each of which is optionally mono- or polysubstituted by identical or different substituents, where (in the case of hetaryl) optionally at least one carbonyl group may be present and where possible substituents in each case are as follows: cyano, carboxyl, halogen, nitro, acetyl, hydroxy, amino, SCN, SF$_5$, tri-$(C_1-C_4)$-alkylsilyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, $(C_1-C_4)$-haloalkyl-$(C_3-C_6)$-cycloalkyl, halo-$(C_3-C_6)$-cycloalkyl, cyano-$(C_3-C_6)$-cycloalkyl, $(C_1-C_4)$-alkyl, $(C_1-C_4)$-haloalkyl, $(C_1-C_4)$-cyanoalkyl, $(C_1-C_4)$-hydroxyalkyl, hydroxycarbonyl-$(C_1-C_4)$-alkoxy, $(C_1-C_4)$-alkoxycarbonyl-$(C_1-C_4)$-alkyl, $(C_1-C_4)$-alkoxy-$(C_1-C_4)$-alkyl, $(C_2-C_4)$-alkenyl, $(C_2-C_4)$-haloalkenyl, $(C_2-C_4)$-cyanoalkenyl, $(C_3-C_6)$-cycloalkyl-$(C_2)$-alkenyl, $(C_2-C_4)$-alkynyl, $(C_2-C_4)$-haloalkynyl, $(C_2-C_4)$-cyanoalkynyl, $(C_1-C_4)$-alkoxy, $(C_1-C_4)$-haloalkoxy, $(C_1-C_4)$-cyanoalkoxy, $(C_1-C_4)$-alkoxycarbonyl-$(C_1-C_4)$-alkoxy, $(C_1-C_4)$-alkoxy-$(C_1-C_4)$-alkoxy, $(C_1-C_4)$-alkoxyimino, $(C_1-C_4)$-haloalkoxyimino, $(C_1-C_4)$-alkylthio, $(C_1-C_4)$-haloalkylthio, $(C_1-C_4)$-alkoxy-$(C_1-C_4)$-alkylthio, $(C_1-C_4)$-alkylthio-$(C_1-C_4)$-alkyl, $(C_1-C_4)$-alkylsulfinyl, $(C_1-C_4)$-haloalkylsulfinyl, $(C_1-C_4)$-alkoxy-$(C_1-C_4)$-alkylsulfinyl, $(C_1-C_4)$-alkylsulfinyl-$(C_1-C_4)$-alkyl, $(C_1-C_4)$-alkylsulfonyl, $(C_1-C_4)$-haloalkylsulfonyl, $(C_1-C_4)$-alkoxy-$(C_1-C_4)$-alkylsulfonyl, $(C_1-C_4)$-alkylsulfonyl-$(C_1-C_4)$-alkyl, $(C_1-C_4)$-alkylsulfonyloxy, $(C_1-C_4)$-haloalkylsulfonyloxy, $(C_1-C_4)$-alkylcarbonyl, $(C_1-C_4)$-haloalkylcarbonyl, $(C_1-C_4)$-alkylcarbonyloxy, $(C_1-C_4)$-alkoxycarbonyl, $(C_1-C_4)$-haloalkoxycarbonyl, aminocarbonyl, $(C_1-C_4)$-alkylaminocarbonyl, $(C_1-C_4)$-haloalkylaminocarbonyl, di-$(C_1-C_4)$-alkylaminocarbonyl, $(C_2-C_4)$-alkenylaminocarbonyl, di-$(C_2-C_4)$-alkenylaminocarbonyl, $(C_3-C_6)$-cycloalkylaminocarbonyl, $(C_1-C_4)$-alkylsulfonylamino, $(C_1-C_4)$-alkylamino, di-$(C_1-C_4)$-alkylamino, $(C_1-C_4)$-haloalkylamino, $(C_3-C_6)$-cycloalkylamino, aminosulfonyl, $(C_1-C_4)$-alkylaminosulfonyl, di-$(C_1-C_4)$-alkylaminosulfonyl, $(C_1-C_4)$-alkylsulfoximino, aminothiocarbonyl, $(C_1-C_4)$-alkylaminothiocarbonyl, di-$(C_1-C_4)$-alkylaminothiocarbonyl, $(C_1-C_4)$-haloalkylaminothiocarbonyl, $(C_3-C_6)$-cycloalkylaminothiocarbonyl, $(C_1-C_4)$-alkylcarbonylamino, $(C_1-C_4)$-haloalkylcarbonylamino, $(C_1-C_4)$-alkylcarbonyl-$(C_1-C_4)$-alkylamino, $(C_1-C_4)$-haloalkylcarbonyl-$(C_1-C_4)$-alkylamino, $(C_3-C_6)$-cycloalkylcarbonylamino, $(C_3-C_6)$-cycloalkylcarbonyl-$(C_1-C_4)$-alkylamino, $(C_1-C_4)$-alkylthiocarbonylamino, $(C_1-C_4)$-haloalkylthiocarbonylamino, $(C_1-C_4)$-alkylthiocarbonyl-$(C_1-C_4)$-alkylamino, $(C_1-C_4)$-haloalkylthiocarbonyl-$(C_1-C_4)$-alkylamino, $(C_3-C_6)$-cycloalkylthiocarbonylamino, $(C_3-C_6)$-cycloalkylthiocarbonyl-$(C_1-C_4)$-alkylamino, hetaryl, oxohetaryl, halohetaryl, halooxohetaryl, cyanohetaryl, cyanooxohetaryl, $(C_1-C_4)$-haloalkylhetaryl or $(C_1-C_4)$-haloalkyloxohetaryl, said process comprising reacting a compound of formula (I)

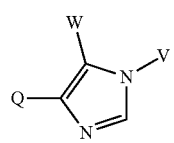

(I)

with an organozinc base of the structure $(NR^aR^b)$—Zn—$R^c$ or $(NR^aR^b)_2$—Zn, in which $R^c$ represents halogen or —O-pivaloyl and $R^a$ and $R^b$ together form a —$(CH_2)_4$—, —$(CH_2)_5$— or —$(CH_2)_2O(CH_2)_2$— group, where each of these groups may optionally be substituted by 1, 2, 3 or 4 $R^d$ radicals and $R^d$ is selected from the group consisting of methyl, ethyl, n-propyl and isopropyl, to give a compound of formula (IVa) or formula (IVb),

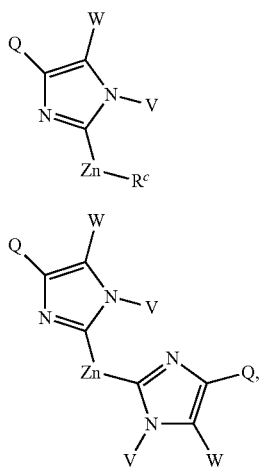

(IVa)

(IVb)

and
b) reacting said compound of formula (IVa) or (IVb) with a compound of the structure Y—X, in which X represents halogen, to give the compound of formula (II).

2. The process according to claim 1, wherein
Q represents a structural element selected from the group consisting of Q1, Q2, Q3, Q4, Q5, Q6, Q7, Q8, Q9, Q13 and Q14,

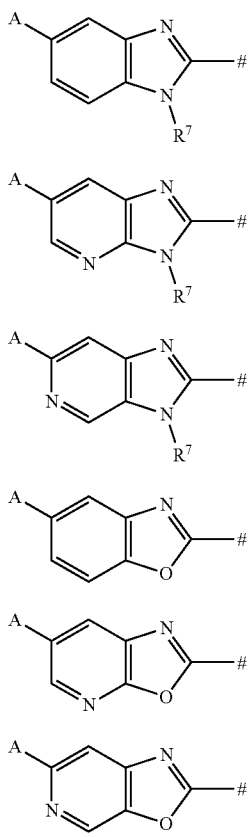

Q1

Q2

Q3

Q4

Q5

Q6

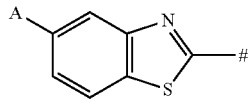

Q7

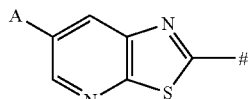

Q8

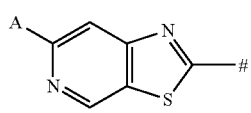

Q9

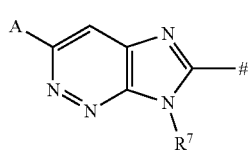

Q13

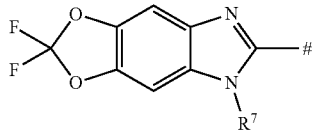

Q14 where
$R^7$ represents $(C_1-C_4)$-alkyl, $(C_1-C_4)$-haloalkyl, $(C_1-C_4)$-alkoxy-$(C_1-C_4)$-alkyl, $(C_1-C_4)$-haloalkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl and
A represents fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulfinyl or trifluoromethylsulfonyl,
W represents halogen or $S(O)_nR^8$, where
$R^8$ represents $(C_1-C_6)$-alkyl, $(C_1-C_6)$-cyanoalkyl, $(C_1-C_6)$-alkoxy-$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_8)$-cycloalkyl and
n represents 0, 1 or 2,
$R^c$ represents halogen, optionally chlorine, bromine or iodine,
V represents $(C_1-C_6)$-alkyl, $(C_1-C_6)$-cyanoalkyl, $(C_1-C_6)$-alkoxy-$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_8)$-cycloalkyl and
Y represents halogen, cyano, $(C_1-C_4)$-alkyl, $(C_1-C_4)$-haloalkyl, $(C_1-C_4)$-alkoxy, $(C_1-C_4)$-haloalkoxy, aminocarbonyl, $(C_1-C_4)$-alkylaminocarbonyl, di-$(C_1-C_4)$-alkylaminocarbonyl, $(C_1-C_4)$-haloalkylaminocarbonyl, $(C_3-C_6)$-cycloalkylaminocarbonyl, amino, $(C_1-C_4)$-alkylamino, $(C_1-C_4)$-haloalkylamino, di-$(C_1-C_4)$-alkylamino, $(C_3-C_6)$-cycloalkylamino, $(C_1-C_4)$-alkylsulfonylamino, $(C_1-C_4)$-alkylcarbonylamino, $(C_1-C_4)$-haloalkylcarbonylamino, $(C_1-C_4)$-alkylcarbonyl-$(C_1-C_2)$-alkylamino, $(C_1-C_4)$-haloalkylcarbonyl-$(C_1-C_2)$-alkylamino, $(C_3-C_6)$-cycloalkylcarbonylamino, $(C_3-$ $C_6$)-cycloalkylcarbonyl-($C_1$-$C_2$)-alkylamino, ($C_2$-$C_4$)-alkenyl, ($C_2$-$C_4$)-haloalkenyl, ($C_2$-$C_4$)-cyanoalkenyl or ($C_3$-$C_6$)-cycloalkyl-($C_2$)-alkenyl, or represents ($C_3$-$C_6$)-cycloalkyl or ($C_5$-$C_6$)-cycloalkenyl, each of which is optionally mono- or polysubstituted by identical or different substituents, possible substituents being in each case: ($C_3$-$C_6$)-cycloalkyl, ($C_1$-$C_4$)-alkyl, ($C_1$-$C_4$)-haloalkyl, ($C_1$-$C_4$)-alkoxy, ($C_1$-$C_4$)-haloalkoxy, halogen or cyano, or represents phenyl, pyridyl, pyrimidyl, pyridazinyl, thiophenyl, furanyl, pyrazolyl, pyrrolyl, thiazolyl, oxazolyl or imidazolyl, each of which is optionally mono- or polysubstituted by identical or different substituents, possible substituents being in each case: cyano, halogen, nitro, acetyl, hydroxy, amino, $SF_5$—, ($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_2$)-alkyl, ($C_2$-$C_4$)-alkenyl, ($C_2$-$C_4$)-haloalkenyl, ($C_2$-$C_4$)-cyanoalkenyl, ($C_3$-$C_6$)-cycloalkyl-($C_2$)-alkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxy-($C_1$-$C_2$)-alkoxy, ($C_1$-$C_4$)-alkoxyimino, ($C_1$-$C_4$)-haloalkoxyimino, ($C_1$-$C_4$)-alkylthio, ($C_1$-$C_4$)-haloalkylthio, ($C_1$-$C_4$)-alkylthio-($C_1$-$C_2$)-alkyl, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_1$-$C_4$)-alkylsulfonyloxy, ($C_1$-$C_4$)-haloalkylsulfonyloxy, ($C_1$-$C_4$)-alkylcarbonyl, ($C_1$-$C_4$)-haloalkylcarbonyl, aminocarbonyl, ($C_1$-$C_4$)-alkylaminocarbonyl, ($C_1$-$C_4$)-haloalkylaminocarbonyl, di-($C_1$-$C_4$)-alkylaminocarbonyl, ($C_3$-$C_6$)-cycloalkylaminocarbonyl, aminothiocarbonyl, ($C_1$-$C_4$)-alkylaminothiocarbonyl, di-($C_1$-$C_4$)-alkylaminothiocarbonyl, ($C_1$-$C_4$)-haloalkylaminothiocarbonyl, ($C_3$-$C_6$)-cycloalkylaminothiocarbonyl, ($C_1$-$C_4$)-alkylsulfonylamino, ($C_1$-$C_4$)-alkylamino, di-($C_1$-$C_4$)-alkylamino, ($C_1$-$C_4$)-haloalkylamino, ($C_3$-$C_6$)-cycloalkylamino, aminosulfonyl, ($C_1$-$C_4$)-alkylaminosulfonyl, di-($C_1$-$C_4$)-alkylaminosulfonyl, ($C_1$-$C_4$)-alkylcarbonylamino, ($C_1$-$C_4$)-haloalkylcarbonylamino, ($C_1$-$C_4$)-alkylcarbonyl-($C_1$-$C_2$)-alkylamino, ($C_1$-$C_2$)-haloalkylcarbonyl-($C_1$-$C_2$)-alkylamino, ($C_3$-$C_6$)-cycloalkylcarbonylamino, ($C_3$-$C_6$)-cycloalkylcarbonyl-($C_1$-$C_2$)-alkylamino, ($C_1$-$C_4$)-alkylthiocarbonylamino, ($C_1$-$C_4$)-haloalkylthiocarbonylamino, ($C_1$-$C_4$)-alkylthiocarbonyl-($C_1$-$C_2$)-alkylamino, ($C_1$-$C_4$)-haloalkylthiocarbonyl-($C_1$-$C_2$)-alkylamino, ($C_3$-$C_6$)-cycloalkylthiocarbonylamino or ($C_3$-$C_6$)-cycloalkylthiocarbonyl-($C_1$-$C_2$)-alkylamino.

3. The process according to claim 2, wherein

Q represents a structural element selected from the group consisting of Q2, Q3, Q4, Q13 and Q14, where $R^7$ represents ($C_1$-$C_4$)-alkyl or ($C_1$-$C_4$)-alkoxy-($C_1$-$C_4$)-alkyl and A represents trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulfinyl or trifluoromethylsulfonyl, W represents halogen or $S(O)_nR^8$, where $R^8$ represents methyl, ethyl, n-propyl or isopropyl and n represents 0, 1 or 2, $R^c$ represents chlorine, V represents methyl, ethyl, n-propyl or isopropyl and Y represents bromine, iodine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, or represents cyclopropyl, cyclobutyl, cyclopentyl, cyclohexyl, cyclopentenyl or cyclohexenyl, each of which is optionally mono- or disubstituted by identical or different substituents, possible substituents being in each case: methyl, ethyl, n-propyl, isopropyl, cyclopropyl, difluoromethyl, trifluoromethyl, cyano, fluorine or chlorine, or represents phenyl, pyridin-2-yl, pyridin-3-yl, pyridin-4-yl, pyrimidin-5-yl, pyridazin-3-yl, pyridazin-4-yl, thien-2-yl, thien-3-yl, 1,3-thiazol-5-yl, 1H-imidazol-1-yl, 1H-imidazol-2-yl, 1H-imidazol-5-yl, 1H-pyrazol-1-yl, 1H-pyrazol-3-yl, 1H-pyrazol-4-yl, 1H-pyrazol-5-yl, 1H-pyrrol-1-yl, 1H-pyrrol-2-yl, 1H-pyrrol-3-yl or 1-cyclohexenyl, each of which is optionally mono-, di- or trisubstituted by identical or different substituents, possible substituents being in each case: cyano, fluorine, chlorine, methyl, cyclopropyl, cyanomethyl, cyanoisopropyl, cyanocyclopropyl, trifluoromethyl, trifluoroethyl or aminocarbonyl.

4. The process according to claim 2, wherein

Q represents the structural element Q3 or Q13, where $R^7$ represents methyl or ethyl, and A represents trifluoromethyl or pentafluoroethyl, W represents $S(O)_nR^8$, where $R^8$ represents ethyl and n represents 0 or 2, $R^c$ represents chlorine, V represents methyl or ethyl, optionally methyl, and Y represents bromine, 5-cyanopyridin-2-yl or 6-chloropyridazin-3-yl.

5. The process according to claim 1, wherein the organozinc base is a compound of formula (VI)

$$(TMP)_xZnCl_{2-x},\qquad(VI)$$

in which x represents the number 1 or 2.

6. The process according to claim 1 wherein the organozinc base is present in conjunction with an alkali metal halide or alkaline earth metal halide, optionally lithium chloride and/or magnesium chloride.

7. The process according to claim 1, wherein a) is conducted at a temperature between 0° C. and 110° C.

8. The process according to claim 1, wherein X represents bromine or iodine.

9. The process according to claim 1, wherein Y represents halogen.

10. The process according to claim 9, wherein the compound X—Y is an elemental halogen, optionally $F_2$, $Cl_2$, $Br_2$ or $I_2$.

11. The process according to claim 1, wherein Y does not represent halogen.

12. The process according to claim 9, wherein b) is carried out at a temperature between 0° C. and 80° C.

13. The process according to claim 11, wherein b) is carried out at a temperature between 0° C. and 120° C.

14. The process according to claim 1, wherein a) and b) are carried out in the presence of an organic solvent, where the solvent is selected from THF and N,N-dimethylformamide (DMF).

15. A compound of formula (IVa)

in which
Q represents a structural element

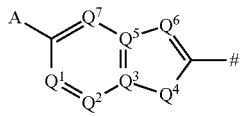

where the symbol # indicates the bond to the rest of the molecule and
$Q^1$ represents N or $CR^6$,
$Q^2$ represents N or $CR^6$,
$Q^3$ represents C,
$Q^4$ represents O, S, N, or $NR^7$,
$Q^5$ represents C,
$Q^6$ represents N and
$Q^7$ represents CH,
$R^6$ represents hydrogen, $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl and
$R^7$ represents $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl or $(C_1-C_4)$-alkylcarbonyl-$(C_1-C_4)$-alkyl,
A represents hydrogen, cyano, halogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, $(C_1-C_4)$-alkylsulfonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulfonylamino, $(C_1-C_4)$-alkylamino, di-$(C_1-C_4)$-alkylamino, aminosulfonyl, $(C_1-C_4)$-alkylaminosulfonyl or di-$(C_1-C_4)$-alkylaminosulfonyl, or
A represents —O—$CF_2$—O— and, together with $Q^1$ and the carbon atom to which it is attached, forms a five-membered ring where $Q^1$ represents carbon,
W represents halogen or $S(O)_nR^8$, where
$R^8$ represents $(C_1-C_6)$-alkyl, $(C_1-C_6)$-cyanoalkyl, $(C_1-C_6)$-alkoxy-$(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl or $(C_3-C_8)$-cycloalkyl and
n represents 0, 1 or 2,
$R^c$ represents halogen or —O-pivaloyl,
V represents $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, cyano-$(C_3-C_8)$-cycloalkyl, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-alkyl, $(C_1-C_6)$-haloalkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl or $(C_1-C_6)$-haloalkoxycarbonyl-$(C_1-C_6)$-alkyl and
Y represents halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, SCN, $(C_1-C_4)$-alkylcarbonyl, $(C_1-C_4)$-haloalkylcarbonyl, $(C_1-C_4)$-alkoxycarbonyl, $(C_1-C_4)$-haloalkoxycarbonyl, $(C_1-C_4)$-alkylaminocarbonyl, di-$(C_1-C_4)$-alkylaminocarbonyl, $(C_1-C_4)$-haloalkylaminocarbonyl, $(C_3-C_6)$-cycloalkylaminocarbonyl, $(C_1-C_4)$-alkylaminothiocarbonyl, di-$(C_1-C_4)$-alkylaminothiocarbonyl, $(C_1-C_4)$-haloalkylaminothiocarbonyl, $(C_3-C_6)$-cycloalkylaminothiocarbonyl, $(C_1-C_4)$-alkylamino, $(C_1-C_4)$-haloalkylamino, di-$(C_1-C_4)$-alkylamino, $(C_3-C_6)$-cycloalkylamino, $(C_1-C_4)$-alkylsulfonylamino, $(C_1-C_4)$-alkylcarbonylamino, $(C_1-C_4)$-haloalkylcarbonylamino, $(C_1-C_4)$-alkylcarbonyl-$(C_1-C_4)$-alkylamino, $(C_1-C_4)$-haloalkylcarbonyl-$(C_1-C_4)$-alkylamino, $(C_3-C_6)$-cycloalkylcarbonylamino, $(C_3-C_6)$-cycloalkylcarbonyl-$(C_1-C_4)$-alkylamino, $(C_1-C_4)$-alkylthiocarbonylamino, $(C_1-C_4)$-haloalkylthiocarbonylamino, $(C_1-C_4)$-alkylthiocarbonyl-$(C_1-C_4)$-alkylamino, $(C_1-C_4)$-haloalkylthiocarbonyl-$(C_1-C_4)$-alkylamino, $(C_3-C_6)$-cycloalkylthiocarbonylamino, $(C_3-C_6)$-cycloalkylthiocarbonyl-$(C_1-C_4)$-alkylamino, $(C_2-C_4)$-alkenyl, $(C_2-C_4)$-haloalkenyl, $(C_2-C_4)$-cyanoalkenyl, $(C_3-C_6)$-cycloalkyl-$(C_2)$-alkenyl, $(C_2-C_4)$-alkynyl or $(C_2-C_4)$-haloalkynyl,
or represents $(C_3-C_6)$-cycloalkyl or $(C_5-C_6)$-cycloalkenyl, each of which is optionally mono- or polysubstituted by identical or different substituents, possible substituents being in each case: $(C_3-C_6)$-cycloalkyl, $(C_1-C_4)$-alkyl, $(C_1-C_4)$-haloalkyl, $(C_1-C_4)$-alkoxy, $(C_1-C_4)$-haloalkoxy, aminocarbonyl, aminothiocarbonyl, halogen or cyano, or represents aryl or hetaryl, each of which is optionally mono- or polysubstituted by identical or different substituents, where (in the case of hetaryl) optionally at least one carbonyl group may be present and where possible substituents in each case are as follows: cyano, carboxyl, halogen, nitro, acetyl, hydroxy, amino, SCN, $SF_5$, tri-$(C_1$-$C_4)$-alkylsilyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, $(C_1$-$C_4)$-haloalkyl-$(C_3$-$C_6)$-cycloalkyl, halo-$(C_3$-$C_6)$-cycloalkyl, cyano-$(C_3$-$C_6)$-cycloalkyl, $(C_1$-$C_4)$-alkyl, $(C_1$-$C_4)$-haloalkyl, $(C_1$-$C_4)$-cyanoalkyl, $(C_1$-$C_4)$-hydroxyalkyl, hydroxycarbonyl-$(C_1$-$C_4)$-alkoxy, $(C_1$-$C_4)$-alkoxycarbonyl-$(C_1$-$C_4)$-alkyl, $(C_1$-$C_4)$-alkoxy-$(C_1$-$C_4)$-alkyl, $(C_2$-$C_4)$-alkenyl, $(C_2$-$C_4)$-haloalkenyl, $(C_2$-$C_4)$-cyanoalkenyl, $(C_3$-$C_6)$-cycloalkyl-$(C_2)$-alkenyl, $(C_2$-$C_4)$-alkynyl, $(C_2$-$C_4)$-haloalkynyl, $(C_2$-$C_4)$-cyanoalkynyl, $(C_1$-$C_4)$-alkoxy, $(C_1$-$C_4)$-haloalkoxy, $(C_1$-$C_4)$-cyanoalkoxy, $(C_1$-$C_4)$-alkoxycarbonyl-$(C_1$-$C_4)$-alkoxy, $(C_1$-$C_4)$-alkoxy-$(C_1$-$C_4)$-alkoxy, $(C_1$-$C_4)$-alkoxyimino, $(C_1$-$C_4)$-haloalkoxyimino, $(C_1$-$C_4)$-alkylthio, $(C_1$-$C_4)$-haloalkylthio, $(C_1$-$C_4)$-alkoxy-$(C_1$-$C_4)$-alkylthio, $(C_1$-$C_4)$-alkylthio-$(C_1$-$C_4)$-alkyl, $(C_1$-$C_4)$-alkylsulfinyl, $(C_1$-$C_4)$-haloalkylsulfinyl, $(C_1$-$C_4)$-alkoxy-$(C_1$-$C_4)$-alkylsulfinyl, $(C_1$-$C_4)$-alkylsulfinyl-$(C_1$-$C_4)$-alkyl, $(C_1$-$C_4)$-alkylsulfonyl, $(C_1$-$C_4)$-haloalkylsulfonyl, $(C_1$-$C_4)$-alkoxy-$(C_1$-$C_4)$-alkylsulfonyl, $(C_1$-$C_4)$-alkylsulfonyl-$(C_1$-$C_4)$-alkyl, $(C_1$-$C_4)$-alkylsulfonyloxy, $(C_1$-$C_4)$-haloalkylsulfonyloxy, $(C_1$-$C_4)$-alkylcarbonyl, $(C_1$-$C_4)$-haloalkylcarbonyl, $(C_1$-$C_4)$-alkylcarbonyloxy, $(C_1$-$C_4)$-alkoxycarbonyl, $(C_1$-$C_4)$-haloalkoxycarbonyl, aminocarbonyl, $(C_1$-$C_4)$-alkylaminocarbonyl, $(C_1$-$C_4)$-haloalkylaminocarbonyl, di-$(C_1$-$C_4)$-alkylaminocarbonyl, $(C_2$-$C_4)$-alkenylaminocarbonyl, di-$(C_2$-$C_4)$-alkenylaminocarbonyl, $(C_3$-$C_6)$-cycloalkylaminocarbonyl, $(C_1$-$C_4)$-alkylsulfonylamino, $(C_1$-$C_4)$-alkylamino, di-$(C_1$-$C_4)$-alkylamino, $(C_1$-$C_4)$-haloalkylamino, $(C_3$-$C_6)$-cycloalkylamino, aminosulfonyl, $(C_1$-$C_4)$-alkylaminosulfonyl, di-$(C_1$-$C_4)$-alkylaminosulfonyl, $(C_1$-$C_4)$-alkylsulfoximino, aminothiocarbonyl, $(C_1$-$C_4)$-alkylaminothiocarbonyl, di-$(C_1$-$C_4)$-alkylaminothiocarbonyl, $(C_1$-$C_4)$-haloalkylaminothiocarbonyl, $(C_3$-$C_6)$-cycloalkylaminothiocarbonyl, $(C_1$-$C_4)$-alkylcarbonylamino, $(C_1$-$C_4)$-haloalkylcarbonylamino, $(C_1$-$C_4)$-alkylcarbonyl-$(C_1$-$C_4)$-alkylamino, $(C_1$-$C_4)$-haloalkylcarbonyl-$(C_1$-$C_4)$-alkylamino, $(C_3$-$C_6)$-cycloalkylcarbonylamino, $(C_3$-$C_6)$-cycloalkylcarbonyl-$(C_1$-$C_4)$-alkylamino, $(C_1$-$C_4)$-alkylthiocarbonylamino, $(C_1$-$C_4)$-haloalkylthiocarbonylamino, $(C_1$-$C_4)$-alkylthiocarbonyl-$(C_1$-$C_4)$-alkylamino, $(C_1$-$C_4)$-haloalkylthiocarbonyl-$(C_1$-$C_4)$-alkylamino, $(C_3$-$C_6)$-cycloalkylthiocarbonylamino, $(C_3$-$C_6)$-cycloalkylthiocarbonyl-$(C_1$-$C_4)$-alkylamino, hetaryl, oxohetaryl, halohetaryl, halooxohetaryl, cyanohetaryl, cyanooxohetaryl, $(C_1$-$C_4)$-haloalkylhetaryl or $(C_1$-$C_4)$-haloalkyloxohetaryl.

16. The compounds of formula (IVb)

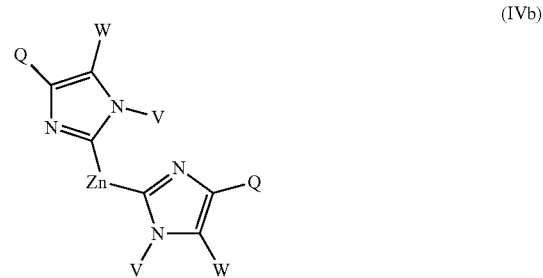

(IVb)

in which

Q represents a structural element

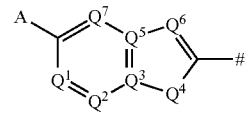

where the symbol # indicates the bond to the rest of the molecule and $Q^1$ represents N or $CR^6$,
$Q^2$ represents N or $CR^6$,
$Q^3$ represents C,
$Q^4$ represents O, S, N, or $NR^7$,
$Q^5$ represents C,
$Q^6$ represents N and
$Q^7$ represents CH,
$R^6$ represents hydrogen, $(C_1$-$C_4)$-alkyl, $(C_1$-$C_4)$-haloalkyl, $(C_1$-$C_4)$-cyanoalkyl, $(C_1$-$C_4)$-alkoxy-$(C_1$-$C_4)$-alkyl, $(C_1$-$C_4)$-haloalkoxy-$(C_1$-$C_4)$-alkyl, $(C_2$-$C_4)$-alkenyl, $(C_2$-$C_4)$-alkenyloxy-$(C_1$-$C_4)$-alkyl, $(C_2$-$C_4)$-haloalkenyloxy-$(C_1$-$C_4)$-alkyl, $(C_2$-$C_4)$-haloalkenyl, $(C_2$-$C_4)$-cyanoalkenyl, $(C_2$-$C_4)$-alkynyl, $(C_2$-$C_4)$-alkynyloxy-$(C_1$-$C_4)$-alkyl, $(C_2$-$C_4)$-haloalkynyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, halo-$(C_3$-$C_6)$-cycloalkyl, $(C_1$-$C_4)$-alkylthio-$(C_1$-$C_4)$-alkyl, $(C_1$-$C_4)$-alkylsulfinyl-$(C_1$-$C_4)$-alkyl, $(C_1$-$C_4)$-alkylsulfonyl-$(C_1$-$C_4)$-alkyl or $(C_1$-$C_4)$-alkylcarbonyl-$(C_1$-$C_4)$-alkyl and
$R^7$ represents $(C_1$-$C_4)$-alkyl, $(C_1$-$C_4)$-haloalkyl, $(C_1$-$C_4)$-cyanoalkyl, $(C_1$-$C_4)$-alkoxy-$(C_1$-$C_4)$-alkyl, $(C_1$-$C_4)$-haloalkoxy-$(C_1$-$C_4)$-alkyl, $(C_2$-$C_4)$-alkenyl, $(C_2$-$C_4)$-alkenyloxy-$(C_1$-$C_4)$-alkyl, $(C_2$-$C_4)$-haloalkenyloxy-$(C_1$-$C_4)$-alkyl, $(C_2$-$C_4)$-haloalkenyl, $(C_2$-$C_4)$-cyanoalkenyl, $(C_2$-$C_4)$-alkynyl, $(C_2$-$C_4)$-alkynyloxy-$(C_1$-$C_4)$-alkyl, $(C_2$-$C_4)$-haloalkynyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, halo-$(C_3$-$C_6)$-cycloalkyl, $(C_1$-$C_4)$-alkylthio-$(C_1$-$C_4)$-alkyl, $(C_1$-$C_4)$-alkylsulfinyl-$(C_1$-$C_4)$-alkyl, $(C_1$-$C_4)$-alkylsulfonyl-$(C_1$-$C_4)$-alkyl or $(C_1$-$C_4)$-alkylcarbonyl-$(C_1$-$C_4)$-alkyl,
A represents hydrogen, cyano, halogen, $(C_1$-$C_4)$-alkyl, $(C_1$-$C_4)$-haloalkyl, $(C_2$-$C_4)$-alkenyl, $(C_2$-$C_4)$-haloalkenyl, $(C_2$-$C_4)$-alkynyl, $(C_2$-$C_4)$-haloalkynyl, $(C_3$-$C_6)$-cycloalkyl, $(C_3$-$C_6)$-cycloalkyl-$(C_3$-$C_6)$-cycloalkyl, $(C_1$-$C_4)$-alkyl-$(C_3$-$C_6)$-cycloalkyl, $(C_1$-$C_4)$-alkoxy, $(C_1$-$C_4)$-haloalkoxy, $(C_1$-$C_4)$-alkoxyimino, $(C_1$-$C_4)$-alkylthio, $(C_1$-$C_4)$-haloalkylthio, $(C_1$-$C_4)$-alkylsulfinyl, $(C_1$-$C_4)$-haloalkylsulfinyl, $(C_1$-$C_4)$-alkylsulfonyl, $(C_1$-$C_4)$-haloalkylsulfonyl, $(C_1$-$C_4)$-alkylsulfonyloxy, $(C_1$-

$C_4$)-alkylcarbonyl, ($C_1$-$C_4$)-haloalkylcarbonyl, aminocarbonyl, ($C_1$-$C_4$)-alkylaminocarbonyl, di-($C_1$-$C_4$)-alkylaminocarbonyl, ($C_1$-$C_4$)-alkylsulfonylamino, ($C_1$-$C_4$)-alkylamino, di-($C_1$-$C_4$)-alkylamino, aminosulfonyl, ($C_1$-$C_4$)-alkylaminosulfonyl or di-($C_1$-$C_4$)-alkylaminosulfonyl, or A represents —O—$CF_2$—O— and, together with $Q^1$ and the carbon atom to which it is attached, forms a five-membered ring where $Q^1$ represents carbon, W represents halogen or $S(O)_n R^8$, where $R^8$ represents ($C_1$-$C_6$)-alkyl, ($C_1$-$C_6$)-cyanoalkyl, ($C_1$-$C_6$)-alkoxy-($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl or ($C_3$-$C_8$)-cycloalkyl and n represents 0, 1 or 2, V represents ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, cyano-($C_3$-$C_8$)-cycloalkyl, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulfinyl-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-alkyl, ($C_1$-$C_6$)-haloalkylsulfonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl or ($C_1$-$C_6$)-haloalkoxycarbonyl-($C_1$-$C_6$)-alkyl and Y represents halogen, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, SCN, ($C_1$-$C_4$)-alkylcarbonyl, ($C_1$-$C_4$)-haloalkylcarbonyl, ($C_1$-$C_4$)-alkoxycarbonyl, ($C_1$-$C_4$)-haloalkoxycarbonyl, ($C_1$-$C_4$)-alkylaminocarbonyl, di-($C_1$-$C_4$)-alkylaminocarbonyl, ($C_1$-$C_4$)-haloalkylaminocarbonyl, ($C_3$-$C_6$)-cycloalkylaminocarbonyl, ($C_1$-$C_4$)-alkylaminothiocarbonyl, di-($C_1$-$C_4$)-alkylaminothiocarbonyl, ($C_1$-$C_4$)-haloalkylaminothiocarbonyl, ($C_3$-$C_6$)-cycloalkylaminothiocarbonyl, ($C_1$-$C_4$)-alkylamino, ($C_1$-$C_4$)-haloalkylamino, di-($C_1$-$C_4$)-alkylamino, ($C_3$-$C_6$)-cycloalkylamino, ($C_1$-$C_4$)-alkylsulfonylamino, ($C_1$-$C_4$)-alkylcarbonylamino, ($C_1$-$C_4$)-haloalkylcarbonylamino, ($C_1$-$C_4$)-alkylcarbonyl-($C_1$-$C_4$)-alkylamino, ($C_1$-$C_4$)-haloalkylcarbonyl-($C_1$-$C_4$)-alkylamino, ($C_3$-$C_6$)-cycloalkylcarbonylamino, ($C_3$-$C_6$)-cycloalkylcarbonyl-($C_1$-$C_4$)-alkylamino, ($C_1$-$C_4$)-alkylthiocarbonylamino, ($C_1$-$C_4$)-haloalkylthiocarbonylamino, ($C_1$-$C_4$)-alkylthiocarbonyl-($C_1$-$C_4$)-alkylamino, ($C_1$-$C_4$)-haloalkylthiocarbonyl-($C_1$-$C_4$)-alkylamino, ($C_3$-$C_6$)-cycloalkylthiocarbonylamino, ($C_3$-$C_6$)-cycloalkylthiocarbonyl-($C_1$-$C_4$)-alkylamino, ($C_2$-$C_4$)-alkenyl, ($C_2$-$C_4$)-haloalkenyl, ($C_2$-$C_4$)-cyanoalkenyl, ($C_3$-$C_6$)-cycloalkyl-($C_2$)-alkenyl, ($C_2$-$C_4$)-alkynyl or ($C_2$-$C_4$)-haloalkynyl, or represents ($C_3$-$C_6$)-cycloalkyl or ($C_5$-$C_6$)-cycloalkenyl, each of which is optionally mono- or polysubstituted by identical or different substituents, possible substituents being in each case: ($C_3$-$C_6$)-cycloalkyl, ($C_1$-$C_4$)-alkyl, ($C_1$-$C_4$)-haloalkyl, ($C_1$-$C_4$)-alkoxy, ($C_1$-$C_4$)-haloalkoxy, aminocarbonyl, aminothiocarbonyl, halogen or cyano, or represents aryl or hetaryl, each of which is optionally mono- or polysubstituted by identical or different substituents, where (in the case of hetaryl) optionally at least one carbonyl group may be present and where possible substituents in each case are as follows: cyano, carboxyl, halogen, nitro, acetyl, hydroxy, amino, SCN, $SF_5$, tri-($C_1$-$C_4$)-alkylsilyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, ($C_1$-$C_4$)-haloalkyl-($C_3$-$C_6$)-cycloalkyl, halo-($C_3$-$C_6$)-cycloalkyl, cyano-($C_3$-$C_6$)-cycloalkyl, ($C_1$-$C_4$)-alkyl, ($C_1$-$C_4$)-haloalkyl, ($C_1$-$C_4$)-cyanoalkyl, ($C_1$-$C_4$)-hydroxyalkyl, hydroxycarbonyl-($C_1$-$C_4$)-alkoxy, ($C_1$-$C_4$)-alkoxycarbonyl-($C_1$-$C_4$)-alkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-cyanoalkenyl, ($C_3$-$C_6$)-cycloalkyl-($C_2$)-alkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxycarbonyl-($C_1$-$C_4$)-alkoxy, ($C_1$-$C_4$)-alkoxy-($C_1$-$C_4$)-alkoxy, ($C_1$-$C_4$)-alkoxyimino, ($C_1$-$C_4$)-haloalkoxyimino, ($C_1$-$C_4$)-alkylthio, ($C_1$-$C_4$)-haloalkylthio, ($C_1$-$C_4$)-alkoxy-($C_1$-$C_4$)-alkylthio, ($C_1$-$C_4$)-alkylthio-($C_1$-$C_4$)-alkyl, ($C_1$-$C_4$)-alkylsulfinyl, ($C_1$-$C_4$)-haloalkylsulfinyl, ($C_1$-$C_4$)-alkoxy-($C_1$-$C_4$)-alkylsulfinyl, ($C_1$-$C_4$)-alkylsulfinyl-($C_1$-$C_4$)-alkyl, ($C_1$-$C_4$)-alkylsulfonyl, ($C_1$-$C_4$)-haloalkylsulfonyl, ($C_1$-$C_4$)-alkoxy-($C_1$-$C_4$)-alkylsulfonyl, ($C_1$-$C_4$)-alkylsulfonyl-($C_1$-$C_4$)-alkyl, ($C_1$-$C_4$)-alkylsulfonyloxy, ($C_1$-$C_4$)-haloalkylsulfonyloxy, ($C_1$-$C_4$)-alkylcarbonyl, ($C_1$-$C_4$)-haloalkylcarbonyl, ($C_1$-$C_4$)-alkylcarbonyloxy, ($C_1$-$C_4$)-alkoxycarbonyl, ($C_1$-$C_4$)-haloalkoxycarbonyl, aminocarbonyl, ($C_1$-$C_4$)-alkylaminocarbonyl, ($C_1$-$C_4$)-haloalkylaminocarbonyl, di-($C_1$-$C_4$)-alkylaminocarbonyl, ($C_2$-$C_4$)-alkenylaminocarbonyl, di-($C_2$-$C_4$)-alkenylaminocarbonyl, ($C_3$-$C_6$)-cycloalkylaminocarbonyl, ($C_1$-$C_4$)-alkylsulfonylamino, ($C_1$-$C_4$)-alkylamino, di-($C_1$-$C_4$)-alkylamino, ($C_1$-$C_4$)-haloalkylamino, ($C_3$-$C_6$)-cycloalkylamino, aminosulfonyl, ($C_1$-$C_4$)-alkylaminosulfonyl, di-($C_1$-$C_4$)-alkylaminosulfonyl, ($C_1$-$C_4$)-alkylsulfoximino, aminothiocarbonyl, ($C_1$-$C_4$)-alkylaminothiocarbonyl, di-($C_1$-$C_4$)-alkylaminothiocarbonyl, ($C_1$-$C_4$)-haloalkylaminothiocarbonyl, ($C_3$-$C_6$)-cycloalkylaminothiocarbonyl, ($C_1$-$C_4$)-alkylcarbonylamino, ($C_1$-$C_4$)-haloalkylcarbonylamino, ($C_1$-$C_4$)-alkylcarbonyl-($C_1$-$C_4$)-alkylamino, ($C_1$-$C_4$)-haloalkylcarbonyl-($C_1$-$C_4$)-alkylamino, ($C_3$-$C_6$)-cycloalkylcarbonylamino, ($C_3$-$C_6$)-cycloalkylcarbonyl-($C_1$-$C_4$)-alkylamino, ($C_1$-$C_4$)-alkylthiocarbonylamino, ($C_1$-$C_4$)-haloalkylthiocarbonylamino, ($C_1$-$C_4$)-alkylthiocarbonyl-($C_1$-$C_4$)-alkylamino, ($C_1$-$C_4$)-haloalkylthiocarbonyl-($C_1$-$C_4$)-alkylamino, ($C_3$-$C_6$)-cycloalkylthiocarbonylamino, ($C_3$-$C_6$)-cycloalkylthiocarbonyl-($C_1$-$C_4$)-alkylamino, hetaryl, oxohetaryl, halohetaryl, halooxohetaryl, cyanohetaryl, cyanooxohetaryl, ($C_1$-$C_4$)-haloalkylhetaryl or ($C_1$-$C_4$)-haloalkyloxohetary.

17. The compound of formula (IVa) according to claim 15, wherein said compound is present complexed with one or more salts, wherein the salts are alkali metal halides or alkaline earth metal halides, optionally lithium chloride and/or magnesium chloride.

18. The compound of formula (IVb) according to claim 16, wherein said compound is present complexed with one or more salts, wherein the salts are alkali metal halides or alkaline earth metal halides, optionally lithium chloride and/or magnesium chloride.

19. The process according to claim 4, wherein
R$^7$ represents methyl, and
V represents methyl.

* * * * *